United States Patent
Wong et al.

(10) Patent No.: US 11,187,706 B2
(45) Date of Patent: Nov. 30, 2021

(54) METHOD AND KIT FOR DETECTION OF ANTI-ZIKA VIRUS ANTIBODIES

(71) Applicant: Health Research, Inc., Menands, NY (US)

(72) Inventors: Susan J. Wong, Glenmont, NY (US); Pei-Yong Shi, Galveston, TX (US)

(73) Assignees: THE BOARD OF REGENTS OF THE UNIVERSITY OF TEXAS SYSTEM, Austin, TX (US); HEALTH RESEARCH, INC., Menands, NY (US)

(*) Notice: Subject to any disclaimer, the term of this patent is extended or adjusted under 35 U.S.C. 154(b) by 0 days.

(21) Appl. No.: 16/435,787

(22) Filed: Jun. 10, 2019

(65) Prior Publication Data

US 2019/0293660 A1   Sep. 26, 2019

Related U.S. Application Data

(63) Continuation of application No. 15/812,174, filed on Nov. 14, 2017, now Pat. No. 10,317,413.

(60) Provisional application No. 62/438,681, filed on Dec. 23, 2016, provisional application No. 62/421,694, filed on Nov. 14, 2016.

(51) Int. Cl.
*G01N 33/68* (2006.01)
*G01N 33/569* (2006.01)
*G01N 33/543* (2006.01)

(52) U.S. Cl.
CPC ..... *G01N 33/6854* (2013.01); *G01N 33/5432* (2013.01); *G01N 33/54313* (2013.01); *G01N 33/56983* (2013.01); *G01N 2800/26* (2013.01); *Y02A 50/30* (2018.01)

(58) Field of Classification Search
CPC .......... G01N 33/6854; G01N 33/5432; G01N 33/54313; G01N 33/56983; G01N 2800/26; Y02A 50/30
See application file for complete search history.

(56) References Cited

U.S. PATENT DOCUMENTS

| | | |
|---|---|---|
| 7,351,547 B2 | 4/2008 | Wong et al. |
| 7,384,785 B2 | 6/2008 | Wong et al. |
| 8,968,874 B2 | 3/2015 | Chandler et al. |
| 9,213,034 B2 | 12/2015 | Walker et al. |
| 9,376,613 B2 | 6/2016 | Chandler et al. |
| 2006/0115896 A1* | 6/2006 | Wong ............... G01N 33/56983 435/345 |
| 2019/0298818 A1* | 10/2019 | Kinney ................. A61K 39/12 |

FOREIGN PATENT DOCUMENTS

| WO | 2017192756 A1 | 11/2017 |
|---|---|---|
| WO | WO2018053478 A1 | 3/2018 |

OTHER PUBLICATIONS

Pyke AT, Daly MT, Cameron JN, Moore PR, Taylor CT, Hewitson GR, Humphreys JL, Gair R. Imported Zika Virus Infection from the Cook Islands into Australia, 2014. PLOS Currents Outbreaks. Jun. 2, 2014 . Edition 1.*
Cao-Lormeau VM, Blake A, Mons S, et al. Guillain-Barre Syndrome outbreak associated with Zika virus infection in French Polynesia: a case-control study. Lancet. 2016;387(10027):1531-1539.*
Beck C, Despres P, Paulous S, et al. A High-Performance Multiplex Immunoassay for Serodiagnosis of Flavivirus-Associated Neurological Diseases in Horses. Biomed Res Int. 2015;2015:678084.*
Charrel RN, Leparc-Goffart I, Pas S, et al. Background review for diagnostic test development for Zika virus infection. Bulletin of the World Health Organization (WHO). 94:574-584D. Pub Online Feb. 10, 2016.*
Powell RL, Ouellette I, Lindsay RW, et al. A Multiplex Microsphere-Based Immunoassay Increases the Sensitivity of SIV-Specific Antibody Detection in Serum Samples and Mucosal Specimens Collected from Rhesus Macaques Infected with SIVmac239. Biores Open Access. 2013;2(3):171-178.*
Stenger RM, Smits M, Kuipers B, Kessen SF, Boog CJ, van Els CA. Fast, antigen-saving multiplex immunoassay to determine levels and avidity of mouse serum antibodies to pertussis, diphtheria, and tetanus antigens. Clin Vaccine Immunol. 2011;18(4):595-603.*
Muller DA, Young PR. The flavivirus NS1 protein: molecular and structural biology, immunology, role in pathogenesis and application as a diagnostic biomarker. Antiviral Res. May 2013;98(2):192-208. Epub Mar. 21, 2013.*
Stettler K, Beltramello M, Espinosa DA, Graham V, Cassotta A, Bianchi S, Vanzetta F, Minola A, Jaconi S, Mele F, Foglierini M, Pedotti M, Simonelli L, et al. Specificity, cross-reactivity, and function of antibodies elicited by Zika virus infection. Science. Aug. 19, 2016;353(6301):823-6. Epub Jul. 14, 2016.*

(Continued)

*Primary Examiner* — Rachel B Gill

(57) ABSTRACT

Provided is a method of detecting the presence of an anti-Zika virus (ZIKV) antibody in a sample, including contacting a sample with a suspension having a plurality of microspheres wherein individual microspheres are conjugated to a peptide and the peptide includes a ZIKV peptide selected from the group including ZIKV NS1, ZIKV NS5, and ZIKV envelope protein, forming a first incubated suspension by incubating said sample with said suspension to permit binding of anti-ZIKV antibodies present in the sample to said microspheres, forming a second incubated suspension by contacting said first incubated suspension with an anti-ZIKV antibody detecting-reagent to permit binding of the anti-ZIKV antibody detecting reagent to said microspheres, removing from the second incubated suspension anti-ZIKV antibody detecting-reagent molecules that are not bound to said microspheres, and detecting the presence of anti-ZIKV antibody detecting-reagent molecules in the second incubated suspension. Also provided is a kit containing reagents and compositions for performing the foregoing method.

10 Claims, 2 Drawing Sheets

(56) References Cited

OTHER PUBLICATIONS

Schleiss, "Congenital Cytomegalovirus Infection: Improved Understanding of Maternal Immune Responses that Reduce the Risk of Transplacental Transmission," Nov. 2017, pp. 1666-1669, Clinical Infectious Diseases Editorial Commentary, vol. 65.

Tanimura et al., "Universal Screening with Use of Immunoglobulin G Avidity for Congenital Cytomegalovirus Infection," Nov. 2017, pp. 1652-1658, Clinical Infectious Diseases Major Article, vol. 65.

Wong et al., "Detection of Human Anti-Flavivirus Antibodies with a West Nile Virus Recombinant Antigen Microsphere Immunoassay," Jan. 2004, pp. 65-72, Journal of Clinical Microbiology, vol. 42, No. 1.

Wong et al., "Immunoassay Targeting Nonstructural Protein 5 to Differentiate West Nile Virus Infection from Dengue and St. Louis Encephalitis Virus Infections and from Flavivirus Vaccination," Sep. 2003, pp. 4217-4223, Journal of Clinical Microbiology, vol. 41, No. 9.

Xu et al., "Identifying Candidate Targets of Immune Responses in Zika Virus Based on Homology to Epitopes in Other Flavivirus Species," Nov. 2016, 38 pages, PLOS Currents Outbreaks, Research Article.

Tsai et al., "Distinguishing Secondary Dengue Virus Infection from Zika Virus Infection with Previous Dengue by a Combination of 3 Simple Serological Tests," 2017, pp. 1-8, Clinical Infectious Diseases Major Article.

Avacta Group plc, "Avacta Rapidly Generates Affimer Binders for Zika Virus Diagnostics," Jun. 2016, 2 pages, The Scientist Magazine.

Matheus et al., "Specificity of Dengue NS1 Antigen in ?Differential Diagnosis of Dengue and Z?ika Virus Infection," Sep. 2016, pp. 1691-1693, Emerging Infectious Diseases, www.cdc.gov/eid, Vo. 22, No. 9.

Song et al., "Zika Virus NS1 Structure Reveals Diversity of Electrostatic Surfaces Among Flaviviruses," Apr. 2016, pp. 456-463, Nature Structural & Molecular Biology, vol. 23, No. 5.

Heberling et al.,"Rapid Dot-Immunobinding Assay on Nitrocellulose for Viral Antibodies," Jan. 1986, pp. 109-113, Journal of Clinical Microbiology, vol. 23, No. 1.

Shan et al., "An Infectious cDNA Clone of Zika Virus to Study Viral Virulence, Mosquito Transmission, and Antiviral Inhibitors," Jun. 2016, 23 pages, Cell Host & Microbe, vol. 19.

Garcia et al., "Recognition of Synthetic Oligopeptides from Nonstructural Proteins NSI and NS3 of Dengue-4 Virus by Sera from Dengue Virus-Infected Children," 1997, pp. 466-470, American Journal of Tropical Medicine Hygiene, vol. 56, No. 4.

Zhao et al., "Structural Basis of Zika Virus-Specific Antibody Protection," Aug. 2016, pp. 1016-1027, Cell, vol. 166.

Stettler et al., "Specificity, Cross-Reactivity and Function of Antibodies Elicited by Zika Virus Infection," Jul. 2016, 10 pages, Science Reports, www.science.sciencemag.org.

Shu et al., "Potential Application of Nonstructural Protein NS1 Serotype-Specific Immunoglobulin G Enzyme-Linked Immunosorbent Assay in the Seroepidemiologic Study of Dengue Virus Infection: Correlation of Results with Those of the Plaque Reduction Neutralization Test," May 2002, pp. 1840-1844, Journal of Clinical Microbiology, vol. 40, No. 5.

Basile et al.,. "Multiplex Microsphere Immunoassays for the Detection of IgM and IgG to Arboviral Diseases," Sep. 2013, 16 pages, PLOS One, vol. 8, No. 9.

Chang et al. (2017) Systematic analysis of protein identity between Zika virus and other arthropod-borne viruses, Bull World Health Organ 95:517-525.

Collins et al. (2017) Lack of Durable Cross-Neutralizing Antibodies against Zika Virus from Dengue Virus Infection, Emerging Infectious Diseases, 23:773-781.

Keasey et al. (2017), Antibody Responses to Zika Virus Infections in Environments of Flavivirus Endemicity, Clinical and Vaccine Immunology 24:1-16.

Dowd et al. (2016), Broadly Neutralizing Activity of Zika Virus-Immune Sera Identifies a Single Viral Serotype, Cell Reports 16:1485-1491.

Balasuriya et al., Detection of antibodies to West Nile Virus in euqine sera using microsphere immunoassay, J Vet Diagn Invest. Jul. 2006: 18(4):392-5.

Priyamvada et al., Human Antibody responses after dengue virus infection are hightly cross-reactive to Zika virus, Proc Nati Acad Sci USA Jul. 12, 2016:113(28):7852-7 Epub Jun. 27, 2016.

Centers for Disease Control and Prevention (CDC); Memorandum: Revised diagnostic testing for Zika, chikungunya, and dengue viruses in US Public Health Laboratories. Feb. 7, 2016.

Ng et al., (2014) Development of a Multiplex Bead-Based Assay to Monitor Dengue Virus Seroconversion. In: Padmanabhan R Vasudevan S. (eds) Dengue. Methods in Molecular Biology (Methods and Protocols) vol. 1138. Humana press, New York, NY Online Feb. 20, 2014.

Russell et al, A comparison of concentration methods applied to non-infectious flavivirus recombinant antigens for use in diagnostic serological assays. J. Virol Methods. Oct. 2007; 145(1):62-70 Epub Jun. 14, 2007.

Johnson et al., Validation of a microsphere-based immunoassay for detection of anti-West Nile virus and anti-St. Louis encephalitis virus immunoglobulin m antibodies. Clin Vaccine Immunol. Sep. 14, 2007.

Shan et al., Zika Virus; Diagnosis, Theraeutics, and Vaccine, ACS Infect Dis. Mar. 11, 2016;2(3):170-2. Epub Mar. 3, 2016.

\* cited by examiner

Table 1. Summary of PRNT, IgM-capture ELISA, and multiplex MIA diagnosis[a]

| Specimen group | Number of specimen | PRNT titer (dilution fold) ZIKV | PRNT titer (dilution fold) DENV | ZIKV IgM-capture ELISA (P/N)* >2 Equivocal | ZIKV IgM-capture ELISA (P/N)* >3 Positive | ZIKV E* | ZIKV NS1* | ZIKV NS5* | Combined DENV-1 to -4 NS1* |
|---|---|---|---|---|---|---|---|---|---|
| I | 7 | <10 | <10 | 5 (5/7=71%) | 5 (5/7=71%) | Negative 5 (5/7=71%) | Negative 6 (6/7=86%) | Negative 6 (6/7=86%) | Negative 6 (6/7=86%) |
| II | 9 | <10 | >10 | 6 (6/9=67%) | 6 (6/9=67%) | Positive 9 (9/9=100%) | Negative 7 (7/9=78%) | Negative 9 (9/9=100%) | Positive 8 (8/9=89%) |
| III | 43 | >10 | <10 | 39 (39/43=91%) | 37 (37/43=86%) | Positive 36 (36/43=84%) | Positive 43 (43/43=100%) | Positive 32 (32/43=74%) | Negative 27 (27/43=63%) |
| IV | 95 | >10 | >10 | 72 (72/95=76%) | 60 (60/95=63%) | Positive 94 (94/95=99%) | Positive 95 (95/95=100%) | Positive 69 (69/95=73%) | Positive 91 (91/95=96%) |

FIG. 2

METHOD AND KIT FOR DETECTION OF ANTI-ZIKA VIRUS ANTIBODIES

CROSS-REFERENCE TO RELATED APPLICATIONS

This application claims priority to U.S. provisional application No. 62/421,694, filed Nov. 14, 2016, and this application claims priority to U.S. provisional application No. 62/438,681, filed Dec. 23, 2016, and this application claims priority to U.S. nonprovisional patent application Ser. No. 15/812,174, filed Nov. 14, 2017, the contents of which applications are incorporated by reference in their entireties into the present disclosure.

FIELD OF THE INVENTION

The present disclosure relates to, inter alia, methods for detection of Zika virus infection and compositions of matter and kits for use in performing said method. More particularly, methods for detection of anti-Zika virus antibodies is provided. More particularly still, a method for detecting the presence of anti-Zika virus antibodies, and distinguished from the presence of antibodies to other flaviviruses. Also disclosed are kits for the performance of such methods.

BACKGROUND OF THE INVENTION

Zika virus (ZIKV) belongs to the genus of flavivirus within the family Flaviviridae. Many flaviviruses are significant human pathogens, including ZIKV, yellow fever (YFV), dengue virus (DENV serotypes 1 to 4), Japanese encephalitis virus (JEV), West Nile virus (WNV), and tick-borne encephalitis virus (TBEV). ZIKV is predominantly transmitted by Aedes spp. mosquitoes, which also transmit DENV and YFV, as well as chikungunya virus (an emerging alphavirus). Besides mosquitoes, ZIKV can also be transmitted through maternofetal route, sex, blood transfusion, and organ transplantation. Approximately 80% of the ZIKV infections are asymptomatic. Disease symptoms associated with ZIKV infection include headaches, fever, lethargy, rash, conjunctivitis, myalgia, and arthralgia. Severe diseases of ZIKV infection include neurotropic Guillain-Barre syndrome and congenital microcephaly. The flavivirus genome is a single-strand, positive-sense RNA of approximately 11,000 nucleotides. It contains a 5' untranslated region (UTR), an open-reading frame (ORF), and a 3' UTR. The single ORF encodes a long polyprotein which is processed into ten viral proteins, including three structural proteins—capsid (C), precursor membrane (prM), and envelope (E) —and seven nonstructural proteins (NS1, NS2A, NS2B, NS3, NS4A, NS4B, and NS5).

Diagnosis of ZIKV infection is performed through detection of viral components (e.g., viral RNA, viral proteins, or virus isolation) and detection of host immune response (e.g., antibodies against viral proteins). For viral component-based diagnosis, RT-PCR, immunoassay, and virus isolation detect ZIKV RNA, viral proteins, and live virus, respectively (Lanciotti et al., 2008); among them, RT-PCR is the most popular assay because of its sensitivity and specificity. The viremic phase of ZIKV infection usually lasts for about one week, yet occasionally persists beyond two weeks. Due to the short duration of the viremic phase, the diagnostic window for detection of viral components is narrow. Therefore, host immune response-based assays play an important role, among which enzyme-linked immunosorbent assays (ELISA), such as IgM-capture ELISA (MAC-ELISA), and plaque reduction neutralization test (PRNT) are the two most commonly used serologic assays in ZIKV diagnosis. Conventionally, serologic diagnosis of Zika virus (ZIKV) infection relies mainly upon IgM-capture ELISA which is confounded with the flaw of cross-reactivity among different flaviviruses. Unfortunately, the interpretation of conventional IgM-capture ELISA assays for ZIKV and other flaviviruses are challenging due to the cross-reactive nature of anti-flaviviral antibodies conventionally used in such tests, leading to equivocal diagnostic results. This challenge is confounding Zika diagnosis because (i) many flaviviruses (e.g., ZIKV and DENV) produce similar disease symptoms and (ii) antibodies from patients infected with ZIKV cross-react with other flaviviruses. Consequently, ZIKV IgM-capture ELISA results typically require neutralization tests for confirmation. Furthermore, PRNT is time-consuming, labor-intensive, slow, and low-throughput, and cost-ineffective, impairing attempts at rapid diagnosis to halt or slow spread if infection. Moreover, PRNT still relies upon both virus-specific and cross-reactive epitopes of viral E protein such that the results may be inconclusive with respect to flavivirus infections (Shan et al., 2016a). There is therefore a need to improve the accuracy and speed of serologic diagnosis for flaviviruses, ZIKV in particular.

SUMMARY OF THE INVENTION

The present disclosure relates to, inter alia, a method of detecting the presence of an anti-Zika virus (ZIKV) antibody in a sample, including contacting a sample with a suspension having a plurality of microspheres wherein individual microspheres are conjugated to a peptide and the peptide includes a ZIKV peptide selected from the group including ZIKV NS1, ZIKV NS5, and ZIKV envelope protein, forming a first incubated suspension wherein forming includes incubating said sample with said suspension to permit binding of anti-ZIKV antibodies present in the sample to said microspheres, forming a second incubated suspension wherein forming includes contacting said first incubated suspension with an anti-ZIKV antibody detecting-reagent to permit binding of the anti-ZIKV antibody detecting reagent to said microspheres, removing from the second incubated suspension anti-ZIKV antibody detecting-reagent molecules that are not bound to said microspheres, and detecting the presence of anti-ZIKV antibody detecting-reagent molecules in the second incubated suspension.

In some embodiments, the method includes individual microspheres conjugated to ZIKV peptides that differ from ZIKV peptides to which other individual microspheres are conjugated, and the ZIKV peptides are selected from ZIKV NS1, ZIKV NS5, and ZIKV envelope protein, and any two of the foregoing.

In other embodiments, different ZIKV peptides are ZIKV NS1 and ZIKV NS5. In some embodiments, individual microspheres are conjugated to ZIKV NS1, and in other embodiments individual microspheres are conjugated to ZIKV NS5. In some embodiments, some microspheres are conjugated to ZIKV Envelope protein, some microspheres are conjugated to ZIKV NS1, and some microspheres are conjugated to ZIKV NS5. In further embodiments, some microspheres are conjugated to ZIKV Envelope protein and some microspheres are conjugated to ZIKV NS1.

In other embodiments, the sample includes a biological sample from a subject and the biological sample is selected from the group including bodily fluid, blood, serum, plasma, saliva, tears, feces, semen, mucous, tissue, tissue homogenate, cellular extract, spinal fluid, and any combination of two or more of the foregoing. In other embodiments, the subject is a human.

In other embodiments, detecting includes measuring an autofluorescence signal emitted by an anti-ZIKV antibody-detecting reagent, an autofluorescence signal emitted by a microsphere, or an autofluorescence signal emitted by an anti-ZIKV antibody-detecting reagent and an autofluorescence signal emitted by a microsphere.

Some embodiments further include detecting the presence of an antibody to a Dengue virus (DENV) protein in a sample, wherein the protein comprises NS1 and the DENV comprises DENV1, DENV2, DENV3, DENV4, or any combination of two or more of the foregoing. For example, some microspheres may be conjugated to DENV1 NS1, some microspheres may be conjugated to DENV2 NS1, some microspheres may be conjugated to DENV3 NS1, and some microspheres may be conjugated to DENV4 NS1. In further embodiments, some microspheres may be conjugated to ZIKV Envelope protein, some microspheres may be conjugated to ZIKV NS1, some microspheres may be conjugated to ZIKV NS5, some microspheres may be conjugated to DENV1 NS1, some microspheres may be conjugated to DENV2 NS1, some microspheres may be conjugated to DENV3 NS1, and some microspheres may be conjugated to DENV4 NS1. In still further embodiments, some microspheres may be conjugated to ZIKV Envelope protein, some microspheres may be conjugated to ZIKV NS1, some microspheres may be conjugated to DENV1 NS1, some microspheres may be conjugated to DENV2 NS1, some microspheres may be conjugated to DENV3 NS1, and some microspheres may be conjugated to DENV4 NS1.

In another aspect, provided is a kit for detecting the presence of an anti-Zika virus (ZIKV) antibody in a sample, including a plurality of microspheres wherein individual microspheres are conjugated to a peptide and the peptide comprises a ZIKV peptide selected from the group consisting of ZIKV NS1, ZIKV NS5, and ZIKV envelope protein. In some embodiments, the kit includes individual microspheres conjugated to one of two or three different ZIKV peptides which differ from ZIKV peptides to which other microspheres are conjugated to, and the different ZIKV peptides are ZIKV NS1, ZIKV NS5, and ZIKV envelope protein, or any two of the foregoing. In some embodiments, the different ZIKV peptides are ZIKV NS1 and ZIKV NS5. In other embodiments, the different ZIKV peptides are ZIKV envelope protein, ZIKV NS1, and ZIKV NS5. In further embodiments, the different ZIKV peptides are ZIKV envelope protein and ZIKV NS1. In still further embodiments, the kit may further include individual microspheres conjugated to one of two or more different DENV peptides which differ from DENV peptides to which other microspheres are conjugated to, and the different DENV peptides are DENV1 NS1, DENV2 NS1, DENV3, NS1, or DENV4 NS1. For example, a kit may include microspheres with the following peptides conjugated thereto: ZIKV NS1, ZIKV NS5, ZIKV Envelope protein, DENV1 NS1, DENV2 NS2, DENV3 NS3, and DENV4 NS4. In some examples, a kit may contain a subset of the foregoing. For example, a kit may contain microspheres with the following peptides conjugated thereto: ZIKV NS1, ZIKV Envelope protein, DENV1 NS1, DENV2 NS2, DENV3 NS3, and DENV4 NS1. In yet other embodiments, a kit may contain any combination of any two or more of the foregoing microspheres. For example, in some embodiments, the different ZIKV peptides are ZIKV NS1 and ZIKV NS5. In other embodiments, the different ZIKV peptides are ZIKV envelope protein, ZIKV NS1, and ZIKV NS5. In further embodiments, the different ZIKV peptides are ZIKV Envelope protein and ZIKV NS1.

In other embodiments, individual microspheres are conjugated to ZIKV NS1. In still other embodiments, individual microspheres are conjugated to ZIKV NS5. In still other embodiments, the kit includes an anti-ZIKV antibody-detecting reagent.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements. The foregoing and other objects, features, and advantages of the invention are apparent from the following detailed description taken in conjunction with the accompanying drawings in which:

FIG. 2 shows a Table (Table 5) of a summary of PRNT, IgM-capture ELISA, and multiplex MIA diagnosis.

DETAILED DESCRIPTION OF THE INVENTION

Figure 1:
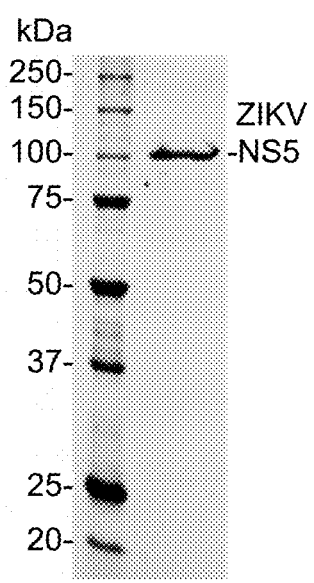
FIG. 1 shows SDS-PAGE analysis of recombinant ZIKV NS5 protein. Full-length NS5 of ZIKV was expressed in an *E. coli* system, and purified through affinity followed by size-exclusion chromatography (see details in Materials and Methods). The recombinant protein was analyzed on a 12% Mini-PROTEAN® TGX Stain-Free™ Protein Gel (Bio-rad).

Aspects of an invention disclosed herein and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating some embodiments, are given by way of illustration only, and are not by way of limitation. Various substitutions, modifications, additions and/or arrangements within the spirit and/or scope of the underlying inventive concepts will be apparent to those skilled in the art from this disclosure.

Disclosed herein is a method for detecting the presence of anti-ZIKV antibodies in a sample, overcoming shortcomings of the prior art. Conventionally, detection of anti-ZIKV antibodies in a sample may require a high volume of sample, may take longer than several hours to perform, may be of low sensitivity resulting in a failure to detect a presence of anti-ZIKV antibodies in a sample, and low selectivity resulting in evidence of a presence of anti-ZIKV antibodies in a sample when no such antibodies are present. Such shortcomings may pose difficulties in accurate detection of the presence of anti-ZIKV antibodies in a sample. According to the present disclosure, small volumes of sample may be used to generate high-probability detection of anti ZIKV-antibodies in a sample.

In one aspect, disclosed is a method for detecting the presence of anti-Zika virus antibodies, such as in a sample from a subject. Such detection may indicate current or prior infection with ZIKV. In particular, the presence of antibodies to the NS5 protein of ZIKV may be detected. The presence of different antibody types, including IgG, IgM, or both, may be accomplished in accordance with the present disclosure. As would be understood by skilled artisans, the presence of different antibody types following a subject's exposure to ZIKV or other flaviviruses follows different time frames, with IgM antibodies to particular antigens being produced sooner after infection than IgG antibodies to said antigens. In various embodiments, detection of one, the other, both, and/or other types of antibodies to ZIKV-derived antigens may provide an indication of a time frame of a subject's exposure to ZIKV relative to when a sample was obtained from the subject. For example, presence of IgM anti-ZIKV antibodies may signify more recent exposure while presence of IgG anti-ZIKV antibodies may signify less recent exposure.

In another aspect, presence of antibodies to ZIKV NS5 may be performed. ZIKV NS5 protein is encoded for by nucleotides 7668-10376 of the ZIKV genome (GenBank number KU955593.1; Shan et al., 2016, Cell Host & Microbe 19:891-900). This sequence, and the peptide product thereof, ZIKV NS5 peptide, differ from the genetic and peptide sequences of NS5 for other viruses, including flaviviruses. For example, NS5 of DENV1-4 differ from ZIKV NS5. As disclosed herein, affinity of antibodies to ZIKV NS5 produced by a subject subsequent to exposure to ZIKV may differ from the affinity of said antibodies to NS5 protein of other viruses, such as DENV or other flaviviruses. The detection of the presence of an anti-ZIKV NS5 antibody in a subject on the basis of whether said antibody binds to ZIKV NS5 may therefore signify that the subject was exposed to ZIKV as distinguished from having been exposed to DENV. Specifically, identifying antibodies in a subject that bind ZIKV NS5 in accordance with the present disclosure indicates that the subject was exposed to ZIKV and may be distinguished from an indication that said subject was exposed to DENV, or other viruses such as other flaviviruses.

In another aspect, presence of antibodies to ZIKV NS1 may be detected. ZIKV NS1 protein is encoded for by nucleotides 2490-3545 of the ZIKV genome (see, e.g., GenBank accession number KU955593.1; Shan et al., 2016, Cell Host & Microbe 19:891-900). This sequence, and the peptide product thereof, ZIKV NS1 peptide, differ from the genetic and peptide sequences of NS1 for other viruses, including flaviviruses. For example, NS1 of DENV1-4 differ from ZIKV NS1. Gene and peptide sequence of NS1 for each of DENV1-4 also differ from each other. The complete genomes of DENV1, DENV2, DENV3, and DENV4 are known (see, e.g., GenBank accession numbers NC_001477.1, NC_001474.2, NC_001475.2, and NC_002640.1, respectively). As disclosed herein, affinity of antibodies to ZIKV NS1 produced by a subject subsequent to exposure to ZIKV differs from the affinity of said antibodies to NS1 protein of other viruses, such as DENV1-4 or other flaviviruses. Nucleotide sequences for DENV1-4 NS1, and the amino acid sequences of such proteins, is known (see, e.g., GenBank accession numbers NP_722461.1, NP_739584.2, YP_001531169.2, and NP_740318.1 for DENV1 NS1, DENV2 NS1, DENV3 NS1, and DENV4 NS1, respectively).

In another aspect, presence of antibodies to a flavivirus envelope protein may be detected. ZIKV envelope peptide amino acid sequence is amino acids 291-792 of ZIKV polyprotein (GenBank accession number AAV34151). Envelope protein of other strains of ZIKV may also be used, as may Envelope proteins from other flaviviruses, such as DENV1 envelope protein, DENV2 envelope protein, DENV3 envelope protein, or DENV1 envelope protein, given the highly conserved amino acid sequences of envelope protein among these viruses and strains thereof.

As further disclosed herein, affinity of antibodies to DENV1 NS1, DENV2 NS1, DENV3 NS1, or DENV4 NS1 produced by a subject subsequent to exposure to DENV1-4, respectively, may differ from the affinity of said antibodies to NS1 protein of other viruses, such as DENV serotypes to which the subject was not exposed, or other flaviviruses. The detection of the presence of an anti-ZIKV NS1 antibody in a subject on the basis of whether said antibody binds to ZIKV NS1 may therefore signify that the subject was exposed to ZIKV as distinguished from having been exposed to DENV1-4. Furthermore, the detection of the presence of an anti-DENV1 NS1, -DENV2 NS1, -DENV3 NS1, or -DENV4 NS1 antibody in a subject on the basis of whether said antibody binds to DENV1 NS1, -DENV2 NS1, -DENV3 NS1, or -DENV4 NS1, respectively, may therefore signify that the subject was exposed to DENV1, DENV2, DENV3, or DENV4, respectively, as distinguished from having been exposed to another serotype of DENV, ZIKV, or to another flavivirus. Specifically, as disclosed herein, identifying antibodies in a subject that bind ZIKV NS1 in accordance with the present disclosure indicates that the subject was exposed to ZIKV and may be distinguished from an indication that said subject was exposed to DENV, or other viruses such as other flaviviruses. And, as disclosed herein, identifying antibodies in a subject that bind to DENV1 NS1, -DENV2 NS1, -DENV3 NS1, or -DENV4 NS1 in accordance with the present disclosure indicates that the subject was exposed to DENV1, DENV2, DENV3, or DENV4, respectively, and may be distinguished from an indication that said subject was exposed to another serotype of DENV, or to ZIKV or another flavivirus.

Antibodies produced in response to ZIKV exposure that have affinity for ZIKV Envelope protein (E) may also have affinity for E protein of other flaviviruses, such as DENV or other types of flaviviruses. Similarities of the peptide sequences and/or conformations of E protein of different flaviviruses may result in the production of antibodies that are cross-reactive to various flaviviruses. If a subject has been exposed to ZIKV, the subject may produce antibodies that have affinity not only for ZIKV E protein but also for E protein of other flaviviruses, including DENV. Likewise, a subject who has been exposed to DENV1-4 may produce antibodies with affinity for E protein of other flaviviruses. Detection in a subject of an antibody with affinity for ZIKV E protein may signify that the subject was exposed to ZIKV, DENV1, DENV2, DENV3, DENV4, or another flavivirus. And, detection in a subject of an antibody with affinity for DENV1 E, DENV2 E, DENV3 E, or DENV4 E may signify that the subject was exposed to ZIKV, DENV1, DENV2, DENV3, DENV4, or another flavivirus.

As further disclosed herein, in one embodiment, detection of multiple different antibodies may be performed on a given sample or samples from a given subject or subjects. In some embodiments, a sample from a subject may be tested for the presence of an antibody with affinity for ZIKV NS1, ZIKV NS5, ZIKV E, DENV1 NS1, DENV2 NS1, DENV3 NS1, DENV4 NS1, or any combination of two or more of the foregoing. In one non-limiting example, a sample from a subject may be tested for the presence of antibodies to ZIKV NS5, ZIKV NS1, ZIKV E, DENV1 NS1, DENV2 NS1, DENV3 NS1, and DENV4 NS1. In another non-limiting example, a sample from a subject may be tested for the presence of antibodies to ZIKV NS1, ZIKV E, DENV1 NS1, DENV2 NS1, DENV3 NS1, and DENV4 NS1. The presence of IgG and IgM antibodies to the foregoing antigens may be tested. If a subject has been exposed to ZIKV but not to other flaviviruses, IgG antibodies, IgM antibodies, or both, to ZIKV NS1, ZIKV NS5, and ZIKV E may be detected. If the subject has been exposed to DENV1-4, antibodies to DENV1-4 NS1 may be detected, as well as to ZIKV E owing to the similarities between ZIKV E and DENV E and cross-reactivity of antibodies thereto. If a subject has been exposed to both ZIKV and DENV, antibodies to ZIKV NS1, ZIKV NS5, ZIKV E, DENV1 NS1, DENV2 NS1, DENV3 NS1, and DENV4 NS1 may all be detected in a sample or samples from said subject.

In a particular embodiment, presence or absence of anti-ZIKV NS5 antibodies may be detected in a sample from a subject. As disclosed herein, high selectivity of anti-ZIKV NS5 antibodies for ZIKV NS5 relative to NS5 or other proteins from other flaviviruses, such as DENV, corresponds to low cross-reactivity of anti-ZIKV NS5 antibodies for other flaviviruses. Similarly, as disclosed herein, low cross-reactivity of antibodies produced in response to exposure to flaviviruses other than ZIKV, such as DENV, to ZIKV NS5 results from selectivity of antibodies produced in response to expose to said other viruses relative to ZIKV NS5. Detection of the presence of an anti-ZIKV NS5 antibody in a sample from a subject as disclosed herein indicates that the subject has been exposed to ZIKV. The absence of anti-ZIKV NS5 antibodies in a sample from a subject may signify that the subject was not exposed to NS5, even if the subject was exposed to another virus, such as another flavivirus such as DENV.

In another particular embodiment, presence or absence of anti-ZIKV NS1 antibodies may be detected in a sample from a subject. As disclosed herein, high selectivity of anti-ZIKV NS1 antibodies for ZIKV NS1 relative to NS1 or other proteins from other flaviviruses, such as DENV, corresponds to low cross-reactivity of anti-ZIKV NS1 antibodies for other flaviviruses. Similarly, as disclosed herein, low cross-reactivity of antibodies produced in response to exposure to flaviviruses other than ZIKV, such as DENV, to ZIKV NS1 results from selectivity of antibodies produced in response to expose to said other viruses relative to ZIKV NS1. Detection of the presence of an anti-ZIKV NS1 antibody in a sample from a subject as disclosed herein indicates that the subject has been exposed to ZIKV. The absence of anti-ZIKV NS1 antibodies in a sample from a subject may signify that the subject was not exposed to NS1, even if the subject was exposed to another virus, such as another flavivirus such as DENV.

In another particular embodiment, presence or absence of anti-ZIKV envelope protein antibodies may be detected in a sample from a subject. In particular examples, presence or absence of anti-ZIKV NS1, anti-ZIKV NS5, anti-ZIKV envelope protein, anti-DENV1 NS1, anti-DENV2 NS1, anti-DENV3 NS1, and anti-DENV4 NS1 may all be detected in a sample from a subject. In another example, presence or absence of anti-ZIKV NS1, anti-ZIKV envelope protein, anti-DENV1 NS1, anti-DENV2 NS1, anti-DENV3 NS1, and anti-DENV4 NS1 may all be detected in a sample from a subject.

In some embodiments, for each and every of the anti-flaviviral protein antibodies disclosed herein, an assay for detection thereof may generate some level of signal indicating presence of reactive antibody in a sample from a subject known not to have been exposed to a or the flaviviruses of interest. Such background signal is known by those skilled in this field to occur and is attributable to some baseline reactivity of sample constituents with a test antigen used as disclosed herein for identifying presence of an anti-flaviviral antibody. Conventionally, an average level of such background may be determined for a given assay against which detection results for a tested subject may be compared to determine whether a given antibody is present. For example, a number of subjects known or believed not to have been exposed to ZIKV or DENV may be tested for the presence of anti-ZIKV and anti-DENV protein antibodies as disclosed herein and an average level of background reactivity of assays as disclosed herein may be determined for a given assay.

For subsequent testing of a subject who may or may not express anti-ZIKV or anti-DENV protein antibodies, a sample taken from such subject may be tested in an assay as disclosed herein and results compared to an average from tests of subjects known or believed not to have been exposed to such flaviviruses. In some instances, a level of detection signal some degree or amount above an average background level of expression may be selected as minimum level qualifying for evincing presence of a given anti-flaviviral protein antibody in a sample from a subject. If a subject is tested for the presence of antibodies against one or more of the foregoing flaviviral proteins and the level of detection signifying presence of any one or more of such antibodies falls below, or above, such cutoff value, then such antibodies may be determined not to have been detected, or to have been detected, respectively, in such sample. In some examples, a cutoff value may be a certain degree above an average level of background signal detected in subjects known or believed not to have been exposed to the flaviviruses in question. For example, a cutoff may be a number of standard deviations above such mean background. A cutoff value may be one, two, or three standard deviations above mean background expression, meaning that antibody to a given flaviviral protein is determined to have been detected for a sample when an assay yields a given level of signal signifying such presence. Cutoff levels may be determined on an anti-flaviviral protein antibody by anti-flaviviral protein antibody basis, as well as on an assay-by-assay basis.

In some embodiments, if a test detects presence of anti-flaviviral proteins, a test may be repeated at a later date and comparing indications that such antibodies were detected at different tests performed. For example, presence or absence of an IgG antibody, or an IgM antibody, or both types of antibodies, to one or more of the flaviviral proteins disclosed herein, may be detected. For example, IgM antibodies to ZIKV envelope and ZIKV NS1, may be detected. Such results may indicate current or recent infection with ZIKV, such as in approximately the past 21 days, as would detection of IgM antibodies to ZIKV NS5. In another example, IgG antibodies to ZIKV envelope and ZIKV NS1, may be detected. Such results may indicate past infection with ZIKV, such as more than 21 days ago, as would detection of IgG antibodies to ZIKV NS5. In still another example, IgM and IgG antibodies to ZIKV envelope and ZIKV NS1, may be detected. Such results may indicate current or recent infection with ZIKV, such as in approximately the past 21 days, as well as past infection, such as more than approximately 21 days ago, as would detection of IgM and IgG antibodies to ZIKV NS5.

In still further embodiments, an avidity assay may be performed to determine whether an anti-flaviviral protein antibody, such as anti-ZIKV envelope protein, anti-ZIKV-NS1, anti-ZIKV NS5, anti-DENV1 NS1, anti-DENV2 NS2, anti-DENV3 NS1, or anti-DENV4 NS1 antibody, or any combination of two or more of the foregoing antibodies, are present and if so, whether they bind to ZIKV envelope protein, ZIKV-NS1, ZIKV NS5, DENV1 NS1, DENV2 NS2, DENV3 NS1, or DENV4 NS1, respectively, with high or low avidity. Detection of high-avidity-binding antibodies that bind to a flaviviral protein with relatively higher avidity (e.g., anti-ZIKV envelope/ZIKV envelope, anti-ZIKV NS1/ZIKV/NS1, anti-ZIKV NS5/ZIKV NS5, anti-DENV1 NS1/DENV1 NS1, anti-DENV2 NS1/DENV2 NSI, anti-DENV3 NS1/DENV3 NS1, or anti-DENV4 NS1/DENV4 binding) may indicate a subject was infected with a given flavivirus as disclosed herein longer ago. Detection of low-avidity-binding antibodies that bind to a flaviviral protein with relatively low avidity (e.g., anti-ZIKV envelope/ZIKV envelope, anti-ZIKV NS1/ZIKV/NS1, anti-ZIKV NS5/ZIKV NS5, anti-DENV1 NS1/DENV1 NS1, anti-DENV2 NS1/DENV2 NSI, anti-DENV3 NS1/DENV3 NS1, or anti-DENV4 NS1/DENV4 binding) may indicate a subject was infected with a given flavivirus more recently, or is currently infected with a given flavivirus. High avidity binding is binding that persists or is still detectable after incubation of a solution of a flaviviral protein or composition such as a polyplex microsphere bound to such antigen as disclosed herein with urea. Urea is known to disrupt low-avidity antigen-antibody association. When a sample is incubated with urea (e.g., 6 M, 8 M, or 10 M urea for 10 minutes) yet presence of anti-flaviviral antibody as disclosed herein is still detected, then high-avidity binding antibodies that bind to a given flaviviral protein have been detected. Detection of absence of antibody after urea incubation indicates absence of high-avidity antibodies. Such avidity testing may be performed for any one, all or any combination of assays for presence of anti-flaviviral protein antibodies.

In some embodiments, presence or absence of a given anti-flaviviral protein antibody or antibodies may indicate that a subject from which a tested sample was taken was previously exposed to or infected with or whose body presently or formerly contained a given flavivirus. For example, if anti-ZIKV envelope protein antibodies are detected in a sample, a subject may be determined to have had or presently have a flavivirus. Given cross-reactivity of an anti-ZIKV envelope protein antibody with envelope proteins of other flaviviruses, such as DENV1, DENV2, DENV3, or DENV4, for example, apparent detection of an anti-ZIKV envelope antibody may signify that the subject has had or has ZIKV, DENV1, DENV2, DENV3, or DENV4. By contrast, as disclosed herein, given selectivity of antibodies to ZIKV NS1 to binding to ZIKV NS1 relative to binding to other flaviviral proteins, such as DENV1 NS1, DENV2 NS1, DENV3 NS1, or DENV4 NS1, which is low, detection of anti-ZIKV NS1 antibodies as disclosed herein signifies that a subject has or has had ZIKV in particular. Similarly, as disclosed herein, given selectivity of antibodies to ZIKV NS5 to binding to ZIKV NS5 relative to binding to other flaviviral proteins, such as DENV1 NS5, DENV2 NS5, DENV3 NS5, or DENV4 NS5, which is low, detection of anti-ZIKV NS5 antibodies as disclosed herein signifies that a subject has or has had ZIKV.

As further disclosed herein, detection of presence multiple different anti-flaviviral protein antibodies combined with detection of absence of e multiple different anti-flaviviral protein antibodies in combination permits possible discriminative determination of presence, or prior presence, of ZIKV, DENV, or both, in a subject. For example, a subject may have had or may have ZIKV but not DENV of any serotype, in which case presence of anti-ZIKV NS1, anti-ZIKV-NS5, and anti-ZIKV envelope protein antibodies may be determined to be present in a sample from such subject, whereas anti-DENV NS1, anti-DENV2 NS1, anti-DENV3 NS1, and anti-DENV4 NS1 antibodies may be determined not to be present in samples from such patients. In another example, a subject may have had or may have a flavivirus of a DENV serotype but not ZIKV, in which case absence of anti-ZIKV NS1 and anti-ZIKV-NS5 antibodies may be detected, and presence of anti-ZIKV envelope protein antibodies, and anti-DENV NS1, anti-DENV2 NS1, anti-DENV3 NS1, and anti-DENV4 NS1 antibodies (depending on which DENV serotype the subject had or has), may be determined to be present in samples from such patients.

The presence of an antibody to a given antigen as disclosed herein may be performed by any of a number of different known methods. In one embodiment, a microsphere immunoassay (MIA) may be used for the detection of an antibody to a given antigen. As would be appreciated by skilled artisans, rapid detection of multiple assays can be performed on low volumes of specimen taken from a subject. In some embodiments, presence of antibodies to one or more of ZIKV NS1, ZIKV NS5, ZIKV E, and NS1 proteins of any of DENV1-4 may be identified in a sample from a subject. In accordance with above-identified differential responsiveness to such testing on the basis of prior viral exposure, different combinations of positive results for particular antibodies may indicate exposure of the subject to ZIKV, DENV1-4, or another flavivirus.

Several options for MIA are available. In some embodiments, flaviviral antigens may be covalently coupled to microbeads and contacted to a sample from a subject, whereupon antibodies to the given antigen present in the sample bind to the bead via the antigen. Subsequent identification of antibody bound to the bead indicates that antibodies to the antigen were present in the sample. In other embodiments, antigen may be coupled to microbeads that have an anti-antigen antibody, or other molecule designed to bind to the antigen such as an affimer or aptamer or other designer ligand, fused thereto via binding to said antibody. Subsequent contacting of the antigen-coupled microbeads to sample from a subject may then be performed as described.

Different sources of viral antigen may be used in accordance with the present disclosure. For example, recombinant peptides whose sequence correspond to the sequence of viral peptide of interest (i.e., ZIKV NS1, ZIKV NS5, ZIKV E, or NS1 proteins of any of DENV1-4) may be synthesized by well-known methods and purified. Recombinant peptides may differ in sequence from native of wild-type flaviviral protein, provided it retains structural, sequential, or conformational properties sufficient to permit recognition by antibodies generated in a subject subsequent to exposure to the corresponding flavivirus. flaviviral protein from which the to which the recombinant Different assays may detect whether antibodies to flaviviral antigen in a sample are IgG antibodies or IgM antibodies, by known methods (e.g., IgG- or IgM-specific methods of detection of anti-flaviviral antigen antibody bound to microbeads, depleting IgG or IgM antibodies from a sample before contacting the sample with antigen-coupled beads, or selecting out IgG or IgM antibodies from a sample and contacting the selected-out antibodies with antigen-coupled microbeads.

In another embodiment, ELISA could be used to detect the presence of antibodies to one or more of ZIKV NS1, ZIKV NS5, ZIKV E, and NS1 proteins of any of DENV1-4 in a sample. For example, anti-IgM antibodies can be coated onto a plate, such as a 96-well or other multi-well plate, and contacted with sample from a subject. IgM antibodies from the sample would become bound to the anti-IgM-coated plate. Following well-known protocols, the IgM-bound plate could then be contacted with antiviral protein of interest, such as ZIKV NS1, ZIKV NS5, ZIKV E, and NS1 proteins of any of DENV1-4, followed by contact with a visualizable antibody to the viral protein. In this way, antiviral protein of interest would, via binding to any antibodies thereto present in the sample that had become bound to the anti-IgM antibody on the plate, be bound to plates that had been exposed to samples from subject that had been exposed to the flavivirus. In turn, such samples would be visualizable, via binding of visualizable anti-flaviviral protein, such as through conjugation with antibodies, fluorophores, or other well-known visualizable or detectable markers. Upon processing to detect presence of the visualizable marker, plates that had been contacted with a sample from a subject that had been exposed to the corresponding flavivirus can be identified and distinguished from those that have not. By performing MAC-ELISA on a sample for antibodies to several different flaviviral proteins (for example, any combination of two or more of ZIKV NS1, ZIKV NS5, ZIKV E, and NS1 proteins of any of DENV1-4), it can be determined whether the subject had been exposed to ZIKV, DENV, and/or another flavivirus.

In another embodiment, a dot blot may be performed to detect the presence of antibodies to one or more of ZIKV NS1, ZIKV NS5, ZIKV E, and NS1 proteins of any of DENV1-4. In dot blotting, a spot or dot of antigen is applied to a membrane, such as nitrocellulose or polyvinyidine fluoride (PVDF). The membrane may then be exposed to a sample from a subject. If the subject has been exposed to a virus that contains the antigen applied to the membrane, such antibodies will couple to a region of the membrane to which the antigen has been applied. The membrane can then be contacted by secondary antibodies (e.g., anti-IgM or anti-IgG) coupled to a visualizable marker (e.g., radiolabel, fluorescent tag, magnetic tag, enzyme, etc.). Visualizable marker is thereby coupled to any region of the membrane to which an antigen recognized by antibodies thereto present in the sample. Upon detection of said marker, presence of antibodies to said antigen in the sample may be determined. In some embodiments, a dot blot analysis may be performed to detect the presence of antibodies to any one or more of ZIKV NS1, ZIKV NS5, ZIKV E, and NS1 proteins of any of DENV1-4, and any combination of two or more of the foregoing. As described above, different permutations of positive and negative results for different anti-flaviviral antigen antibodies suggests that the subject from which the sample was taken was exposed to different flavivirus(es).

In yet another embodiment, immunochromatography may be used to identify the presence of one or more flaviviral antibody in a subject. As one nonlimiting example, and immunochromatographic strip test (ICST) may be used. In such assays, a small strip comprising capillary beds may be exposed to a sample from a subject. Embedded in the strip may be a viral antigen to which antibodies are to be detected. When an aqueous sample is drawn into contact with such antigens following contact with the capillary structure of the strip, the antigens are bound to any antibodies thereto that are present in the sample. The antigen may carry visualizable markers, such as colored latex, gold nanoparticles, or fluorescent or magnetic particles which can be visualized with appropriate readers. Further along the strip, a capture portion containing antibodies to the antigen immobilized to the strip bed may be present, such as in a concentrated region, stripe, or area. As sample continues to migrate along the capillary bed, it encounters the immobilized antibodies of the capture portion. If antibody to the particular antigen were present in the sample, their migration across the capillary bed would have carried bound, visualizable antigen with them, which, in turn, would be immobilized on the capture portion owing to the anti-antigen antibodies immobilized therein. As more antibody accumulates that the capture portion, the visualizable markers become detectable and, when detected, signify the presence of antibody to the antigen of interest.

In some examples, multiple ICST strips, each designed to permit the detection of antibodies to a different flaviviral antigen (e.g., ZIKV NS1, ZIKV NS5, ZIKV E, or NS1 proteins of any of DENV1-4) may be used to test the presence of antibodies to more than one such antigen in a sample. As described above, different permutations of positive and negative results for different anti-flaviviral antigen antibodies suggests that the subject from which the sample was taken was exposed to different flavivirus(es).

As would be appreciated by skilled artisans, modifications of the foregoing methods may be performed in keeping the with present disclosure. Other methods where ZIKV NS1, ZIKV NS5, ZIKV E, DENV1 NS1, DENV2 NS1, DENV3 NS1, DENV4 NS1, or combinations of any two or more of the foregoing, are used to bind antibodies present in a sample, followed by methods used to visualize, detect, quantify, bind, identify, or otherwise record the presence and/or quantity thereof in the sample may be performed, all of which are explicitly intended as embodiments of the present disclosure, of which the foregoing examples are but non-limiting representations of the method disclosed herein. Kits containing reagents used in performing any such method, including reagents, antigens, labeling reagents or labeled antigens or antibodies, microspheres, binding membranes such as nitrocellulose, PVDF, or the like, lateral flow strips, with or without reagents needed for performing the disclosed method included therein, any tubes, vials, needles, or other tools needed for obtaining and/or storing samples, etc., are explicitly included in and considered embodiments of an invention disclosed herein.

As would be understood by skilled artisans, antigens used in any of the foregoing methods may be modified in accordance with standard molecular biology techniques. For example, antigens may be produced with identifiable tags appended thereto to facilitate isolation, identification, concentration, collection, application, or other uses thereof. As one non-limiting example, antigens with histidine tags may be produced to facilitate separation of recombinant antigens from other constituents employed during synthesis thereof, and subsequent concentration of said antigens in a usable form, solvent, diluent, or concentration. Although histidine tags are mentioned here as one non-limiting example, skilled artisans would appreciate that any of a wide variety of such tools could be adapted to and employed with the above-disclosed methods and compositions, without departing from, and hereby explicitly recounted as included within, the method as disclosed herein.

Although non-limiting examples discussed herein include using full-length recombinant flaviviral peptides as antigens, skilled artisans would appreciate that full-length peptides would not necessarily be required for use in all embodiments of the method and compositions disclosed herein. For example, a specific or portions less than full-length viral proteins may be used rather than full-length protein. A portion less than full-length protein to which antibodies produced in response to a subject's exposure to a given flavivirus will bind may be used rather than full-length protein, for example. In some embodiments, a portion less than full-length flaviviral protein to which antibodies produced in response to a subject's exposure to a given flavivirus, but not another flavivirus, will bind may be used. In other examples, portions less than full length protein that bind to antibodies produced in response to either of two or more different flaviviruses may be used.

In yet other embodiments, an antigen with less than total homology to a flaviviral protein, such as ZIKV NS1, ZIKV NS5, ZIKV E, DENV1 NS1, DENV2 NS1, DENV3 NS1, or DENV4 NS1 may be used, as may a combination of any two or more of the foregoing. For example, a recombinant flaviviral protein with an amino acid sequence that corresponds to some but not all of the amino acids in the flaviviral protein to which it corresponds may be used. In some examples, a recombinant flaviviral antigen with 75% or more homology to a corresponding naturally occurring flaviviral protein may be used. In some examples, a flaviviral antigen with between 75%-80% homology, 80%-85% homology, 85%-90% homology, 90%-95% homology, 95%-100% homology, 90%-91% homology, 91%-92% homology, 92%-93% homology, 93%-94% homology, 94%-95% homology, 95%-96% homology, 96%-97% homology, 97%-98% homology, or 99%-100% homology may be used. Several strains of ZIKV have been identified with high levels of homology between their sequences of ZIKV envelope protein, between their sequences of ZIKV NS1, and between their sequences of ZIKV NS5. ZIKV protein sequences homologous to such known strains may be used, within homology ranges as disclosed herein, in accordance with the present disclosure. A recombinant flaviviral antigen with less than 100% homology to a corresponding flaviviral protein to which antibodies produced in response to a subject's exposure to a given flavivirus will bind may be used rather than a recombinant protein with 100% homology. In some embodiments, a recombinant flaviviral protein of less than 100% homology to flaviviral protein to which antibodies produced in response to a subject's exposure to a given flavivirus, but not another flavivirus, will bind may be used. In other examples, a recombinant flaviviral protein of less than 100% homology to flaviviral protein to which antibodies produced in response to a subject's exposure to two or more given flaviviruses may be used.

In other embodiments, an antigen with an amino acid sequence that corresponds to only a portion of a full-length flaviviral protein, such as ZIKV NS1, ZIKV NS5, ZIKV E, DENV1 NS1, DENV2 NS1, DENV3 NS1, or DENV4 NS1 may be used, as may a combination of any two or more of the foregoing. For example, a truncated portion of ZIKV NS1, ZIKV NS5, ZIKV E, DENV1 NS1, DENV2 NS1, DENV3 NS1, or DENV4 NS1, which is recognized by antibodies generated in response to flaviviral infection, may be used. In some embodiments, an antigen may include amino acids not present in naturally occurring flaviviral proteins. For example, as would be understood by skilled artisans, for purposes of antigen synthesis and purification, an antigen may contain an amino acid tag, such as on its C-terminus or its N-terminus, without interfering with the binding thereto of an antibody produced by an individual as a result of flaviviral infection. Many possible such tags ae well-known, including a poly-histidine tag, a myc-tag, a FLAG-tag, an HA-tag, or many others, all of which could be included as part of an antigen and be within the scope of methods and kits as disclosed herein.

A sample may be a biological sample, such as a bodily fluid, blood, serum, plasma, saliva, tears, feces, semen, mucous, tissue, tissue homogenate, cellular extract, or spinal fluid, containing anti-flavivirus antigen antibodies, such as IgG anti-NS5, IgM anti-NS5, IgG anti-E, or IgM anti-E. A subject may be any vertebrate, such as a horse, pig, cow, dog, cat, bat, primate, including human, goat, sheep, deer, rabbit, mouse, rat, chicken or other avian species, or other animal.

EXAMPLES

The following examples are presented to further describe techniques in accordance with the method disclosed herein, but should not be read as limiting, because variations still within the scope of embodiments of the present invention will be apparent to those skilled in the art.

Reagents. Wash buffer and phosphate buffered saline pH 7.4, 0.05% sodium azide (PBS-TN) were purchased from Sigma (Sigma Aldrich, St. Louis, Mo.). Chemicals, 1-Ethyl-3-(3-dimethylaminopropyl) carbodiimide hydrochloride (EDC) and N-hydroxysulfosuccinimide (sulfo-NHS), were supplied by Pierce Chemicals (Pierce, Rockford, Ill.). Microspheres, calibration microspheres, and sheath fluid were obtained from Luminex Corporation (Luminex Corp., Austin, Tex.).

Serum samples. Studies were performed on serum from de-identified clinical specimens submitted to New York State Department of Health for ZIKV IgM-capture ELISA and Arbovirus MIA testing.

Positive and negative serum controls. ZIKV positive control sera were defined as positive titer from a Plaque Reduction Neutralization Test of 90% inhibition ($PRNT_{90}$) against ZIKV, but negative $PRNT_{90}$ titer against DENV. Similarly, DENV positive control sera were defined as positive $PRNT_{90}$ titer against DENV, but negative $PRNT_{90}$ titer against ZIKV. Negative control sera were defined as no ZIKV $PRNT_{90}$ titer as well as negative Arbovirus MIA result using WNV E protein as the diagnostic antigen (Wong et al., 2003). PBN (consisting of PBS, 1% BSA, 0.05% Sodium Azide, pH 7.4) was used as a blank control.

Expression and purification of recombinant ZIKA NS5 protein. The cDNA fragment encoding the full-length NS5 of ZIKV was amplified from an infectious clone pFLZIKV (Shan et al., 2016b), fused with a C-terminal (His)6-tag, and cloned into vector pNIC28-Bsa4 (GenBank accession EF198106), resulting in plasmid construct pNIC28-ZIKA-NS5. ZIKA NS5 protein was expressed in *E. coli* Rosetta 2 pLysS *E. coli* (Stratagene) and purified using a method as previously described (Zhao et al., 2015) with some modifications. Briefly, transformed *E. coli* cells was induced by 0.3 mM isopropyl β-D-1-thiogalactopyranoside (IPTG) when the cell density reached OD600 of 0.6~0.8. After incubation at 18° C. for 16 h, the cells were harvested, re-suspended in buffer A (20 mM Tris-HCl, pH 8.5, 550 mM NaCl, 10% glycerol, 5 mM β-mercaptoethanol, 10 mM imidazole, and 0.5×EDTA-free protease inhibitor cocktail) by sonication. The lysate was clarified by centrifugation at 40,000 g for 30 min at 4° C. The resulting supernatant was loaded onto a HisTrap Fast Flow column (GE Healthcare). The protein was eluted using a linear gradient of imidazole concentration from 40 to 500 mM. The fractions containing ZIKA NS5-(His)6 protein were pooled, concentrated, and further purified by gel filtration using a HiLoad Superdex 200 16/60 column (GE Healthcare) in buffer B (20 mM Na-Hepes, pH 8.2, 500 mM NaCl, 10% glycerol, and 5 mM DTT). The peak fractions containing ZIKA NS5-(His)6 protein were pooled and concentrated to approximately 1~2 mg/ml before storage at −80° C.

Recombinant ZIKV E, NS1, and DENV NS1 proteins. Recombinant ZIKV E, NS1, and DENV-1 to DENV-4 NS1 proteins were purchased from Meridian (Meridian Life Science, Inc., Memphis, Tenn.). All Meridian recombinant proteins were produced in insect cells and purified by affinity chromatography method. Purified proteins were analyzed by 12.5% sodium dodecyl sulfate (SDS)-polyacrylamide gel electrophoresis (PAGE) and stored in PBS pH 7.4.

Conjugation of protein antigens to microsphere Luminex beads. Recombinant proteins were covalently coupled to Luminex MicroPlex Microspheres carboxylated polystyrene microparticles following a previously reported protocol (Wong et al., 2003). Briefly, 50 µg of purified protein was used to couple to the surface of 6.25×106 microspheres in a two-step carbodiimide process. (i) Activation of microspheres. Microspheres were activated with 10 µl of N-hydroxysuccinimide (sulfo-NHS) (50 mg/ml) followed by 10 µl of 1-ethyl-3-(3-dimethylamino-propyl) carbodiimide-HCl (50 mg/ml). Microspheres were then incubated for 20 min at room temperature with gentle vortexing at 10-min intervals. (ii) Coupling of recombinant proteins. Each recombinant protein was added to the activated microspheres with distinct fluorescence. Protein-microsphere mixtures were incubated for 3 h in the dark on a LabTech tube rotator (Barstead/Thermolyne, Dubuque, Iowa). The microspheres were then washed twice by centrifugation and resuspended in 1.0 ml PBS-TN [phosphate buffered saline pH 7.4, 0.05% sodium azide, 1% bovine serum albumin (BSA)]. The protein coupled microsphere were then stored at 4° C.

Multiplex reagent preparation and microsphere immunofluorescence assay (MIA) procedure. All reagent dilutions and assays were carried out in PBS-TN (phosphate buffered saline pH 7.4, 0.05% sodium azide, 1% BSA) (Sigma Aldrich, St. Louis, Mo.). The bead mixture consisted of seven beads, each coupled with a different flavivirus recombinant protein. Three bead sets contained ZIKV E (Meridian), NS1 (Meridian), and NS5 (described above). Four other bead sets contained NS1 proteins from DENV-1 to -4. The bead sets were stored at 4° C. in the dark and diluted 1:100 directly in PBS-TN before use. Biotin conjugated goat anti-human IgG/A/M affinity purified secondary antibody (Life Technologies, Grand Island, N.Y.) was diluted 1:8000 in PBS-TN directly before use. Streptavidin-R-phycoerythrin (1 mg/ml SA-PE, Life Technologies, Grand Island, N.Y.) was diluted 1:100 in PBS-TN before use. All serum samples were stored at −80° C. Samples were thawed and diluted 1:100 in PBS-TN right before use. Diluted samples were used within 1 h post dilution.

A 96-well MultiScreenHTS BV 1.2 µm Filter Plate (Millipore Billerica, Mass.) was wetted with 100 µl PBS-TN and washed once with washing buffer (PBS, 0.05% Tween 20, pH 7.4; Sigma Aldrich, St. Louis, Mo.). Samples (50 µl) were dispensed in each well to which 50 µl bead mixture was added. The plate was incubated in the dark on a shaker for 30 min and washed three times with 190 µl washing buffer. After addition of 50 µl conjugate antibody, samples were incubated in the dark on a shaker for 30 min and washed three times with 190 µl wash buffer. After adding detection reagent SA-PE (50 µl), samples were incubated in the dark on a shaker for 30 min, washed twice with 190 µl wash buffer, and transferred to a flat bottom 96-well plate (Corning Incorporated, Kennebunk, Me.). Analysis was performed using a Luminex 100 Analyzer configured to count 100 beads per bead class and a 100 µl sample size.

For avidity assays, urea at a final concentration of 8 M was added to a sample during incubation of the sample with microspheres bound to a given antigen and urea incubation was for 10 min. Another microsphere-sample was incubated in the absence of urea in parallel. Median fluorescence intensity of each sample was then determined. An Avidity Index was identified, which is a ratio of median fluorescence intensity of urea-treated sample divided by median fluorescence intensity of non-urea treated sample, times 100. An IgG Avidity Index of less than or equal to 30% indicates infection occurred within the past 65 days, or early acute infection. An IgG Avidity Index of from 31% to 60% indicates infection occurred between 65 and 190 days ago, or late acute infection. An avidity index of greater than or equal to 60% indicates infection occurred more than 190 days ago. In samples in which anti-Zika NS1 or anti-Zika NS5 antibodies are detected in addition to anti-DENV antigen antibodies, avidity testing assists in determining whether one infection preceded the other, or whether one or the other infection is current or more acute than the other. For example, a subject may have a high Avidity Index for anti-DENV antigens and a low Avidity Index for anti-ZIKV antigens, indicating recent or current ZIKV infection and past DENV infection.

Results

Rationale of assay platform and antigen selection. The MIA platform for assay development was used because of (i) its multiplex capability to simultaneously detect antibodies against a number of viral proteins, (ii) rapid assay turn-around time in <4 h, and (iii) low specimen volume requirement (10 µl serum). This is in contrast with the well-established IgM-capture ELISA platform that requires >2 days of the assay turnaround time. For antigen selection, three recombinant ZIKV proteins were employed for the multiplex assay: E, NS1, and NS5. ZIKV E protein was included to sensitively detect viral infection; however, due to the cross-reactive nature of E antibodies among flaviviruses, an E-positive signal does not confirm ZIKV infection. ZIKV NS1 and NS5 proteins were included to improve assay specificity through detection of virus-type specific antibodies. In addition, recombinant DENV NS1 proteins from each of the four serotypes were included for testing virus-type specificity. All antigens, except ZIKV NS5, were commercially purchased. ZIKV NS5 was cloned, expressed, and purified to >95% homogeneity. See FIG. 1. SDS-PAGE analysis of recombinant ZIKV NS5 protein. Full-length NS5 of ZIKV was expressed in an E. coli system, and purified through affinity followed by size-exclusion chromatography (see details in Materials and Methods). The recombinant protein was analyzed on a 12% Mini-PROTEAN® TGX Stain-Free™ Protein Gel (Bio-rad).

Establishment of multiplex MIA. Seven recombinant antigens described above (ZIKV E, NS1, NS5, and DENV-1 to -4 NS1) were individually conjugated to microsphere beads, each with a distinct fluorescent signature. A mixture of seven antigen-conjugated beads were reacted with patient serum and quantified by anti-human immunoglobulins (reactive with IgG, IgM, and IgA) with a red fluorescent phycoerythrin. To establish the cutoff level for each antigen, we assayed 20 presumed human sera from healthy individuals in the context of multiplex MIA. The results revealed cutoff values (defined as mean plus three times standard deviations) to be 1363, 284, 1905, 746, 549, 339, and 655 for ZIKV E, NS1, NS5, and DENV-1, -2, -3, and -4 NS1, respectively. These cutoff values were used to determine positive (>cutoff) and negative (<cutoff) when diagnosing patient specimens.

Stratification of patient sera. A well-defined set of patient specimens may be used to develop and verify the multiplex assay. A total of 154 patient sera with known ZIKV and DENV PRNT results were selected for assay development. Based on the PRNT results, patient sera were categorized into four distinct groups. Group I specimens (7 patients; Table 1) were both ZIKV- and DENV-negative, as defined by PRNTs <10 for both viruses.

TABLE 1

Type I specimens with neither ZIKV nor DENV infection defined by PRNT*

| ZIKV PRNT Cutoff 10 | DENV PRNT Cutoff 10 | ZIKV IgM-capture ELISA Cutoff 2 & 3 | ZIKV E Cutoff 1363 | ZIKV NS1 Cutoff 284 | ZIKV NS5 Cutoff 1905 | DENV-1 NS1 Cutoff 746 | DENV-2 NS1 Cutoff 549 | DENV-3 NS1 Cutoff 339 | DENV-4 NS1 Cutoff 655 |
|---|---|---|---|---|---|---|---|---|---|
| <10 | <10 | 0.2 | 1189 | 167 | 573 | 1200 | 935 | 100 | 450 |
| <10 | <10 | 0.5 | 1415 | 155 | 308 | 220 | 259 | 61 | 96 |
| <10 | <10 | 0.9 | 195 | 54 | 1128 | 87 | 51 | 230 | 175 |
| <10 | <10 | 1.9 | 366 | 91 | 1900 | 306 | 216 | 168 | 136 |
| <10 | <10 | 1.9 | 7742 | 4619 | 4267 | 127 | 105 | 113 | 275 |
| <10 | <10 | 3.8 | 178 | 69 | 534 | 235 | 141 | 113 | 211 |
| <10 | <10 | 11.6 | 1001 | 53 | 211 | 418 | 509 | 75 | 125 |

*The table is sorted with increasing value of IgM-capture ELISA result.

Group II specimens (9 patients; Table 2) were ZIKV-negative and DENV-positive, as defined by ZIKV PRNT<10 and DENV PRNT>10.

TABLE 2

Type II specimens with DENV only infection defined by PRNT*

| ZIKV PRNT Cutoff 10 | DENV PRNT Cutoff 10 | ZIKV IgM-capture ELISA Cutoff 2 & 3 | ZIKV E Cutoff 1363 | ZIKA NS1 Cutoff 284 | ZIKV NS5 Cutoff 1905 | DENV-1 NS1 Cutoff 746 | DENV-2 NS1 Cutoff 549 | DENV-3 NS1 Cutoff 339 | DENV-4 NS1 Cutoff 655 |
|---|---|---|---|---|---|---|---|---|---|
| <10 | 20 | 0.19 | 9131 | 234 | 170 | 5375 | 1579 | 3091 | 1442 |
| <10 | 40 | 0.60 | 7145 | 211 | 331 | 9101 | 2831 | 5415 | 3740 |
| <10 | 80 | 1.5 | 11139 | 2514 | 249 | 9145 | 6658 | 10609 | 14941 |
| <10 | 160 | 1.5 | 9596 | 1806 | 177 | 7486 | 5198 | 8241 | 11867 |
| <10 | 640 | 1.5 | 5381 | 46 | 227 | 5323 | 860 | 2235 | 1352 |
| <10 | 80 | 1.6 | 8071 | 67 | 554 | 6862 | 510 | 1765 | 658 |
| <10 | 40 | 5.1 | 6017 | 51 | 1473 | 98 | 50 | 99 | 165 |
| <10 | 160 | 5.8 | 7756 | 38 | 968 | 4259 | 179 | 582 | 305 |
| <10 | 40 | 77 | 8703 | 106 | 1009 | 8805 | 1511 | 3165 | 1558 |

*The table is sorted with increasing value of IgM-capture ELISA result.

Group III specimens (43 patients; Table 3) were ZIKV-positive and DENV-negative, as defined by ZIKV PRNT>10 and DENV PRNT <10.

TABLE 3

Type III specimens with ZIKV only infection defined by PRNT *

| ZIKV PRNT Cutoff 10 | DENV PRNT Cutoff 10 | ZIKV IgM-capture ELISA Cutoff 2 & 3 | ZIKV E Cutoff 1363 | ZIKA NS1 Cutoff 284 | ZIKV NS5 Cutoff 1905 | DENV-1 NS1 Cutoff 746 | DENV-2 NS1 Cutoff 549 | DENV-3 NS1 Cutoff 339 | DENV-4 NS1 Cutoff 655 |
|---|---|---|---|---|---|---|---|---|---|
| 80 | <10 | 0.6 | 9960 | 5207 | 2624 | 1346 | 1172 | 454 | 744 |
| 320 | <10 | 0.99 | 10692 | 6173 | 1676 | 409 | 531 | 660 | 631 |
| 2560 | <10 | 1.8 | 16318 | 9407 | 10423 | 548 | 737 | 802 | 492 |
| 320 | <10 | 1.9 | 12377 | 6550 | 21510 | 391 | 644 | 927 | 422 |
| 40 | <10 | 2.4 | 858 | 617 | 1401 | 349 | 272 | 249 | 374 |
| 10 | <10 | 2.75 | 2185 | 297 | 1777 | 795 | 729 | 189 | 285 |
| 80 | <10 | 3.04 | 800 | 481 | 227 | 163 | 213 | 118 | 252 |
| 160 | <10 | 3.80 | 9088 | 7010 | 3298 | 438 | 588 | 782 | 459 |
| 320 | <10 | 3.97 | 11272 | 4849 | 2129 | 1556 | 1268 | 250 | 838 |
| 320 | <10 | 4 | 11358 | 4933 | 2179 | 1503 | 1212 | 212 | 735 |
| 320 | <10 | 4.5 | 8592 | 5500 | 4362 | 311 | 455 | 452 | 220 |
| 2560 | <10 | 4.5 | 8592 | 5500 | 4362 | 311 | 455 | 452 | 220 |
| 160 | <10 | 6.2 | 3896 | 3152 | 2524 | 574 | 477 | 203 | 371 |
| 160 | <10 | 7.88 | 5782 | 701 | 574 | 340 | 260 | 125 | 217 |
| 1280 | <10 | 7.9 | 3233 | 5196 | 5865 | 231 | 263 | 315 | 246 |
| 1280 | <10 | 7.9 | 4777 | 6771 | 8260 | 364 | 417 | 508 | 381 |
| 320 | <10 | 8.1 | 8842 | 4811 | 15599 | 214 | 349 | 561 | 276 |
| 320 | <10 | 8.1 | 9768 | 5001 | 18463 | 253 | 405 | 532 | 294 |
| 160 | <10 | 8.29 | 457 | 540 | 930 | 464 | 258 | 204 | 168 |

TABLE 3-continued

Type III specimens with ZIKV only infection defined by PRNT *

| ZIKV PRNT Cutoff 10 | DENV PRNT Cutoff 10 | ZIKV IgM-capture ELISA Cutoff 2 & 3 | ZIKV E Cutoff 1363 | ZIKA NS1 Cutoff 284 | ZIKV NS5 Cutoff 1905 | DENV-1 NS1 Cutoff 746 | DENV-2 NS1 Cutoff 549 | DENV-3 NS1 Cutoff 339 | DENV-4 NS1 Cutoff 655 |
|---|---|---|---|---|---|---|---|---|---|
| 1280 | <10 | 10.9 | 496 | 1010 | 3139 | 102 | 84 | 74 | 108 |
| 160 | <10 | 13.5 | 12420 | 7611 | 1809 | 141 | 195 | 218 | 401 |
| 160 | <10 | 13.5 | 14292 | 8757 | 2491 | 180 | 243 | 265 | 548 |
| 160 | <10 | 13.7 | 7432 | 6664 | 2876 | 90 | 159 | 337 | 149 |
| 40 | <10 | 17 | 536 | 1554 | 2612 | 153 | 202 | 122 | 153 |
| 640 | <10 | 17.70 | 6381 | 7713 | 18520 | 1095 | 1082 | 628 | 419 |
| 640 | <10 | 20.1 | 2474 | 2312 | 2038 | 197 | 205 | 67 | 82 |
| 640 | <10 | 20.18 | 3703 | 1566 | 4269 | 75 | 69 | 314 | 54 |
| 160 | <10 | 22 | 530 | 428 | 679 | 151 | 116 | 110 | 119 |
| 160 | <10 | 22 | 999 | 5442 | 3802 | 217 | 234 | 263 | 86 |
| 320 | <10 | 25 | 7905 | 6814 | 5828 | 244 | 350 | 242 | 166 |
| 320 | <10 | 25.5 | 8518 | 6914 | 6650 | 261 | 378 | 303 | 228 |
| 1280 | <10 | 27 | 8494 | 5334 | 3631 | 102 | 107 | 103 | 274 |
| 1280 | <10 | 27.18 | 10443 | 6998 | 4530 | 157 | 163 | 158 | 407 |
| 640 | <10 | 28 | 3488 | 11213 | 4269 | 290 | 452 | 579 | 62 |
| 640 | <10 | 28.8 | 8741 | 7471 | 3820 | 278 | 492 | 662 | 147 |
| 640 | <10 | 29.9 | 6212 | 4915 | 5969 | 193 | 221 | 288 | 115 |
| 640 | <10 | 30 | 3998 | 3187 | 3867 | 133 | 141 | 158 | 73 |
| 1280 | <10 | 32 | 11745 | 7674 | 4459 | 174 | 49 | 242 | 250 |
| 1280 | <10 | 32.3 | 13259 | 8154 | 4726 | 227 | 309 | 304 | 309 |
| 640 | <10 | 42.1 | 9721 | 7456 | 658 | 143 | 276 | 230 | 139 |
| 2560 | <10 | 47.2 | 16346 | 4928 | 3714 | 149 | 158 | 320 | 60 |
| 320 | <10 | 50.4 | 8250 | 7160 | 638 | 134 | 251 | 215 | 122 |
| 320 | <10 | 65.6 | 3645 | 2785 | 1229 | 52 | 74 | 77 | 79 |

* The table is sorted with increasing value of IgM-capture ELISA result.

Group IV specimens (95 patients; Table 4) were both ZIKV- and DENV-positive, as defined by PRNTs>10 for both viruses.

TABLE 4

Type IV specimens with ZIKV and/or DENV infection(s) defined by PRNT*

| ZIKV PRNT Cutoff 10 | DENV PRNT Cutoff 10 | ZIKV IgM-capture ELISA Cutoff 2 & 3 | ZIKV E Cutoff 1363 | ZIKV NS1 Cutoff 284 | ZIKV NS5 Cutoff 1905 | DENV-1 NS1 Cutoff 746 | DENV-2 NS1 Cutoff 549 | DENV-3 NS1 Cutoff 339 | DENV-4 NS1 Cutoff 655 |
|---|---|---|---|---|---|---|---|---|---|
| 2560 | 320 | 0.3 | 12411 | 3002 | 6118 | 7992 | 5677 | 11340 | 10357 |
| 10 | 40 | 0.40 | 7446 | 285 | 790 | 7714 | 2875 | 5725 | 4420 |
| 320 | 2560 | 0.4 | 15916 | 4164 | 11951 | 10070 | 8345 | 14047 | 13683 |
| 20 | 1280 | 0.41 | 18428 | 802 | 461 | 7969 | 5627 | 10631 | 9581 |
| 80 | 640 | 0.45 | 17887 | 2203 | 665 | 5073 | 3700 | 5778 | 9545 |
| 160 | 640 | 0.45 | 18357 | 2550 | 796 | 5886 | 4181 | 6677 | 10700 |
| 20 | 640 | 0.45 | 17361 | 874 | 551 | 9206 | 6339 | 11251 | 11171 |
| 10 | 80 | 0.49 | 16355 | 1950 | 570 | 10920 | 8275 | 15354 | 11740 |
| 1280 | 2560 | 0.53 | 18809 | 6682 | 650 | 16472 | 10777 | 18272 | 19435 |
| 10 | 160 | 0.53 | 8131 | 844 | 325 | 5142 | 3838 | 7463 | 6020 |
| 1280 | 2560 | 0.56 | 20863 | 6548 | 602 | 16500 | 10369 | 19309 | 19308 |
| 160 | 2560 | 0.62 | 17472 | 3453 | 2503 | 12655 | 2806 | 11109 | 16787 |
| 160 | 2560 | 0.69 | 18220 | 3461 | 2384 | 13241 | 2871 | 12265 | 17857 |
| 2560 | 640 | 0.8 | 18354 | 8434 | 2396 | 382 | 426 | 556 | 309 |
| 640 | 1280 | 1.09 | 16382 | 4065 | 3303 | 11394 | 7116 | 13885 | 7695 |
| 320 | 2560 | 1.3 | 17322 | 4085 | 875 | 15507 | 11175 | 17637 | 16700 |
| 2560 | 320 | 1.41 | 19995 | 6926 | 8456 | 12524 | 11268 | 17951 | 16740 |
| 640 | 1280 | 1.53 | 21501 | 7952 | 3037 | 16148 | 12733 | 19792 | 22445 |
| 320 | 160 | 1.63 | 14009 | 6104 | 1374 | 11801 | 11004 | 17719 | 4475 |
| 320 | 2560 | 1.7 | 19788 | 8615 | 3494 | 16160 | 13589 | 19342 | 20432 |
| 160 | 2560 | 1.8 | 16928 | 3607 | 551 | 14462 | 10561 | 17158 | 15002 |
| 1280 | 1280 | 1.81 | 17896 | 7868 | 2698 | 14294 | 11672 | 17853 | 21180 |
| 320 | 2560 | 1.9 | 20374 | 8309 | 2755 | 16466 | 13975 | 19997 | 20689 |
| 640 | 2560 | 2.1 | 21021 | 12154 | 15783 | 18993 | 14796 | 21073 | 22419 |
| 640 | 2560 | 2.16 | 21035 | 11444 | 13536 | 18240 | 15675 | 21260 | 22412 |
| 5160 | 5120 | 2.3 | 18554 | 6707 | 553 | 12751 | 10464 | 17362 | 20153 |
| 5120 | 1280 | 2.3 | 19606 | 11677 | 11105 | 14953 | 11886 | 18231 | 21051 |
| 5120 | 1280 | 2.32 | 18697 | 9335 | 7705 | 12257 | 9981 | 16633 | 17776 |
| 640 | 1280 | 2.45 | 20559 | 10939 | 21381 | 14675 | 10696 | 18537 | 17415 |

TABLE 4-continued

Type IV specimens with ZIKV and/or DENV infection(s) defined by PRNT*

| ZIKV PRNT Cutoff 10 | DENV PRNT Cutoff 10 | ZIKV IgM-capture ELISA Cutoff 2 & 3 | ZIKV E Cutoff 1363 | ZIKV NS1 Cutoff 284 | ZIKV NS5 Cutoff 1905 | DENV-1 NS1 Cutoff 746 | DENV-2 NS1 Cutoff 549 | DENV-3 NS1 Cutoff 339 | DENV-4 NS1 Cutoff 655 |
|---|---|---|---|---|---|---|---|---|---|
| 2560 | 1280 | 2.5 | 19945 | 9641 | 13280 | 15589 | 13022 | 19484 | 15561 |
| 2560 | 1280 | 2.52 | 18959 | 8035 | 11647 | 14771 | 12827 | 19260 | 13601 |
| 320 | 40 | 2.57 | 9760 | 1309 | 386 | 5967 | 1610 | 2724 | 3719 |
| 160 | 40 | 2.59 | 10893 | 859 | 180 | 3100 | 914 | 1643 | 6687 |
| 160 | 40 | 2.72 | 13602 | 1082 | 205 | 4179 | 1260 | 2191 | 8609 |
| 320 | 40 | 2.99 | 10133 | 1442 | 417 | 6469 | 1696 | 3018 | 4257 |
| 320 | 5120 | 3.13 | 18591 | 7977 | 1050 | 11995 | 9617 | 15868 | 14587 |
| 160 | 320 | 3.53 | 19680 | 5587 | 1681 | 317 | 292 | 543 | 270 |
| 2560 | 2560 | 3.89 | 17268 | 4501 | 5464 | 13748 | 9869 | 17527 | 12169 |
| 5120 | 5120 | 3.99 | 21644 | 10859 | 21825 | 12761 | 9859 | 17755 | 20283 |
| 160 | 320 | 4.02 | 16822 | 6103 | 2070 | 14021 | 10298 | 17324 | 15517 |
| 640 | 1280 | 4.42 | 20593 | 5338 | 1739 | 12752 | 11158 | 18128 | 18042 |
| 1280 | 1280 | 4.43 | 19973 | 8594 | 11143 | 12763 | 11051 | 17739 | 16997 |
| 1280 | 320 | 4.79 | 19355 | 10636 | 9796 | 12751 | 10778 | 18003 | 18073 |
| 640 | 1280 | 4.88 | 16101 | 4858 | 776 | 13093 | 8198 | 14431 | 8430 |
| 2560 | 1280 | 5.01 | 20780 | 12080 | 17177 | 16920 | 13760 | 20359 | 17012 |
| 160 | 640 | 5.1 | 19275 | 6311 | 2744 | 14623 | 12984 | 19646 | 15016 |
| 160 | 640 | 5.34 | 16289 | 5747 | 2635 | 15009 | 11904 | 18826 | 16649 |
| 10 | 80 | 5.47 | 16794 | 1307 | 1328 | 389 | 200 | 346 | 281 |
| 1280 | 640 | 6.05 | 16809 | 6987 | 3429 | 13666 | 12416 | 18579 | 5716 |
| 1280 | 80 | 6.52 | 2111 | 3626 | 1100 | 209 | 289 | 243 | 291 |
| 320 | 160 | 7.04 | 19585 | 2905 | 3390 | 10849 | 5579 | 10368 | 11556 |
| 320 | 160 | 7.04 | 20334 | 3419 | 4461 | 11917 | 6275 | 12136 | 12769 |
| 320 | 80 | 7.32 | 19940 | 2687 | 2942 | 10583 | 5368 | 9833 | 10471 |
| 1280 | 10 | 7.49 | 13338 | 9654 | 6618 | 462 | 650 | 1220 | 700 |
| 1280 | 10 | 7.5 | 12624 | 9195 | 6717 | 341 | 478 | 986 | 514 |
| 2560 | 20480 | 8.3 | 20265 | 9171 | 2720 | 16781 | 12747 | 18712 | 20473 |
| 640 | 5120 | 8.5 | 20671 | 9098 | 7078 | 17100 | 14388 | 18608 | 22061 |
| 640 | 10240 | 9.04 | 21114 | 11671 | 11204 | 19358 | 15223 | 21543 | 22106 |
| 2560 | 320 | 10.16 | 18279 | 9899 | 7213 | 4524 | 3165 | 6948 | 1278 |
| 160 | 640 | 10.90 | 20183 | 7660 | 2078 | 2723 | 2628 | 5909 | 1384 |
| 320 | 640 | 10.99 | 14737 | 4336 | 15626 | 11828 | 9458 | 15927 | 6841 |
| 320 | 2560 | 11.1 | 20977 | 10041 | 2254 | 17295 | 13477 | 19549 | 10638 |
| 640 | 10240 | 11.4 | 20785 | 12169 | 11619 | 18884 | 15119 | 20667 | 21989 |
| 1280 | 2560 | 12 | 19968 | 8988 | 4259 | 17044 | 13238 | 19273 | 22230 |
| 1280 | 2560 | 12.54 | 20467 | 8901 | 3673 | 16470 | 13221 | 19341 | 22846 |
| 320 | 640 | 13 | 20546 | 6045 | 1818 | 15929 | 10974 | 18017 | 3192 |
| 640 | 1280 | 14 | 18531 | 5202 | 1896 | 11359 | 10329 | 16770 | 16440 |
| 640 | 640 | 14.64 | 20336 | 7675 | 1722 | 13716 | 12002 | 18849 | 20055 |
| 320 | 2560 | 15 | 21156 | 10463 | 3187 | 18463 | 14572 | 20246 | 22876 |
| 640 | 2560 | 16 | 20527 | 9862 | 5041 | 16141 | 12408 | 19080 | 21991 |
| 640 | 2560 | 16.29 | 19340 | 9066 | 5185 | 15029 | 11748 | 17407 | 20104 |
| 2560 | 20480 | 17 | 22317 | 6665 | 7447 | 15855 | 10725 | 17403 | 5509 |
| 2560 | 20480 | 17.23 | 17999 | 5738 | 7214 | 13635 | 8930 | 14737 | 5748 |
| 160 | 1280 | 17.41 | 19848 | 8375 | 6839 | 15679 | 13745 | 18998 | 22484 |
| 160 | 160 | 20.73 | 9391 | 6074 | 3340 | 356 | 679 | 566 | 309 |
| 10240 | 320 | 22 | 17752 | 7270 | 4264 | 62 | 156 | 388 | 96 |
| 1280 | 1280 | 22.2 | 20185 | 8584 | 16360 | 16030 | 12594 | 20100 | 10783 |
| 1280 | 20480 | 23 | 20703 | 10096 | 7859 | 18086 | 13614 | 18507 | 21267 |
| 320 | 20 | 23.6 | 9924 | 8081 | 9837 | 113 | 203 | 469 | 231 |
| 1280 | 5120 | 23.69 | 18836 | 8498 | 4119 | 15799 | 12910 | 18325 | 20333 |
| 320 | 10 | 25 | 1061 | 3108 | 2294 | 88 | 89 | 83 | 894 |
| 640 | 640 | 25.23 | 20066 | 9245 | 4529 | 17030 | 14304 | 20372 | 22431 |
| 2560 | 2560 | 26.13 | 21184 | 9524 | 2734 | 15615 | 13845 | 19053 | 22401 |
| 640 | 2560 | 27.9 | 19121 | 3787 | 3230 | 3522 | 3308 | 7426 | 3591 |
| 1280 | 10240 | 29.15 | 19711 | 10327 | 2437 | 16973 | 14262 | 18898 | 20341 |
| 1280 | 2560 | 29.9 | 21902 | 8590 | 3728 | 16006 | 13452 | 20836 | 22510 |
| 640 | 1280 | 30.53 | 18080 | 8675 | 17545 | 16414 | 13525 | 18677 | 14452 |
| 2560 | 640 | 32 | 20207 | 6094 | 11566 | 10231 | 7930 | 14480 | 11206 |
| 640 | 2560 | 33.4 | 20649 | 10126 | 6628 | 16806 | 13194 | 18759 | 22293 |
| 320 | 160 | 35.88 | 4640 | 4268 | 2211 | 294 | 263 | 175 | 169 |
| 320 | 10 | 44.8 | 9837 | 7200 | 2590 | 284 | 253 | 308 | 194 |
| 2560 | 2560 | 46.1 | 19943 | 7114 | 7170 | 15766 | 11664 | 18454 | 8917 |
| 640 | 640 | 47.93 | 2828 | 5437 | 7229 | 334 | 1185 | 1407 | 299 |
| 1280 | 20 | 49.11 | 14063 | 6262 | 6839 | 359 | 291 | 193 | 250 |
| 1280 | 640 | 57 | 19062 | 6018 | 11756 | 12258 | 10914 | 17240 | 17024 |

*The table is sorted with increasing value of IgM-capture ELISA result.

It should be noted that, due to cross-neutralization of antibodies among flaviviruses, group IV specimens could derive from patients who were (i) infected with both ZIKV and DENV, (ii) infected with ZIKV only but had antibodies cross-reactive to DENV, or (iii) infected with DENV only but with antibodies cross-reactive to ZIKV.

Multiplex MIA and IgM-capture ELISA diagnosis. Patient samples were subjected to multiplex MIA and the well-established IgM-capture ELISA (Martin et al., 2000). Tables S1 to S4 summarize the results for groups I to IV specimens, respectively. Each specimen is presented with results from PRNT, IgM-capture ELISA, and multiplex MIA for individual antigens. It should be pointed out that, for IgM-capture ELISA, P/N<2 is defined as negative, P/N 2-3 as equivocal, and P/N>3 as positive. Table 5 in FIG. 2 summarizes the overall diagnostic results. For Table 5 in FIG. 2, results from Tables 1 to 4 are summarized for comparison of PRNT, IgM-capture ELISA, and multiplex MIA diagnosis. For each diagnostic parameter, the total number of samples that were diagnosed as "positive" (greater than cutoff line) or "negative" (less than cutoff line) is indicated, followed by its corresponding percentage of the total number of specimens from that specific specimen group. Percentage (%)=(number of positive or negative specimens/total number of specimen from the specific specimen group)×100%.

For group I specimens (neither ZIKV nor DENV infection), both ZIKV IgM-capture ELISA and E MIA showed 71% negative; the MIA results from ZIKV NS1, ZIKV NS5, and combined DENV-1 to -4 NS1 showed 86% negative. For group II specimens (DENV infection only), ZIKV IgM-capture ELISA showed 67% negative (i.e., 33% cross-reactivity with DENV); ZIKV E and combined DENV-1 to -4 NS1 MIA showed 100% and 89% positive, respectively; in contrast, ZIKV NS1 and NS5 MIA showed 78% and 100% negative, respectively. For group III specimens (ZIKV infection only), ZIKV IgM-capture ELISA showed 86% positive; ZIKV E, NS1, and NS5 MIA showed 84%, 100%, and 74% positive, respectively; whereas combined DENV-1 to -4 NS1 MIA showed 63% negative (i.e., 37% cross-reactivity with ZIKV). For group IV specimens (at least one infection from ZIKV and/or DENV), ZIKV IgM-capture ELISA, E, NS1, NS5, and combined DENV NS1 showed 63%, 99%, 100%, 73%, and 96% positive, respectively. These results enable the following analysis.

(I) Comparison of ZIKV IgM-capture ELISA and E MIA. Compared with IgM-capture ELISA, ZIKV E MIA alone showed equivalent accuracy when diagnosing group III specimens, with 86% and 84% of the samples tested positive from IgM-capture ELISA and E MIA, respectively. When diagnosing group IV specimens, the E MIA showed better sensitivity than IgM-capture ELISA, with 63% and 99% of specimens tested positive, respectively. Two factors may account for this improvement. (i) MIA measures IgG and IgA in addition to IgM, whereas IgM-capture ELISA does not capture IgG and IgA. (ii) The amount of IgM declines after the convalescent phase of ZIKV infection; therefore, specimens (taken long after convalescent phase) may have low levels of IgM and high levels of IgG, which is not detected by the IgM-capture ELISA. Taken together, the results indicate that E MIA alone has equivalent or better sensitivity than IgM-capture ELISA.

(II) Relative specificity of ZIKV E, NS1, and NS5 MIA. Comparison of the results from ZIKV E, NS1, and NS5 MIA demonstrates that antibody response to NS1 and NS5 antigens is more ZIKV-specific than that to E antigen. Specifically, ZIKV E MIA showed 100% cross-reactivity with specimens with DENV only infection from group II, confirming the cross-reactive nature of flavivirus E antibodies. In contrast, ZIKV NS1 MIA showed 14% and 22% false positive results when testing groups I and II specimens, but 100% positive accuracy when analyzing groups III and IV specimens. For ZIKV NS5 MIA, the assay exhibited 14% and 0% false positive results when testing groups I and II specimens, and 74% and 73% positive accuracy when analyzing groups III and IV specimens. The results clearly indicate that inclusion of ZIKV NS1 and NS5 in the MIA could improve the diagnostic accuracy when compared with the MIA that uses E protein alone.

(III) Cross reactivity between DENV/ZIKV NS1 proteins and their antibodies. Although antibody response to ZIKV NS1 is more virus-type specific than that to E protein (see above), we clearly observed cross reactivity between DENV and ZIKV NS1 proteins and their antibodies. Specifically, DENV NS1 MIA showed 89% and 96% positive accuracy when testing groups II and IV specimens, respectively; and 14% and 37% false positive results when testing groups I and III specimens, respectively. The 37% false positive result demonstrates that DENV NS1 cross-reacts to specimens with ZIKV-only-infection. Reciprocally, ZIKV NS1 MIA exhibited 22% false positive when testing specimens with DENV-only-infection from group II. Altogether, the results showed 22-37% cross reactivity between DENV and ZIKV NS1 proteins. The data are in agreement with the recent report that antibodies to NS1 are largely ZIKV-specific.

Conventionally, ZIKV serologic diagnosis is mainly based on IgM-capture ELISA with Emergency Use Authorization (EUA) approval from FDA. There is a need for improved methods for detection of anti-ZIKV antibodies in samples from a subject. As disclosed herein, the diagnostic power of viral envelope protein (that elicits robust, yet cross-reactive antibodies to other flaviviruses) is hereby combined with the differential power of viral nonstructural proteins NS1 and NS5 (that induce more virus-type specific antibodies). Disclosed herein is use of an assay using an MIA format that can shorten assay turnaround time. Over 10,000 sera have been tested by conventional, presently FDA emergency use authorized Zika MAC-ELISA testing. Any such samples presumptive as positive for Zika IgM according to such assay was further tested via PRNT. Approximately 80% of the time such assays resulted in identifying the sample as indicating "undifferentiated flavivirus" (meaning indicating that some flaviviral infection had been present, but not definitively ruling in or out ZIKV or DENV. Further testing on over 3600 of these samples permitted an identification of whether a subject had been infected with ZIKV, DENV, both, or neither, and whether in the past 65 days, past 65-190 days, or more than 190 days ago. As a result, as opposed to high rates of "undifferentiated flavivirus" results, the method disclosed herein permitted confirmatory identification of such specifics of infection in approximately 90% of cases where flaviviral infection was indicated.

Furthermore, an assay disclosed herein was performed on many Zika IgM nonreactive, PCR negative specimens from pregnant women with known dengue history. Nearly half of 199 samples from such pregnant women had evidence of a history of Zika infection at some time according to an assay disclosed herein, combining detection of anti ZIKV E, anti-ZIKV NS1, and anti-DENV1-4 NS1 antibodies. Some pregnant women who are IgM negative to Zika may still deliver an infant at risk of congenital Zika syndrome, indicating the importance of accurate testing such as disclosed herein.

Using over 3600 samples patient samples with known ZIKV and DENV PRNT results, the method was verified and improved ability to distinguish ZIKV infection from DENV infection according to methods and kits as disclosed herein. Embodiments of a method disclosed herein are distinct from the single antigen-based (either E or NS1) diagnostic assays, including the E-based IgM-captured ELISA from InBios (with EUA approval from FDA), NS1-based indirect ELISA from EuroImmun (approved for clinical use in Europe), and NS1-based IgM-capture ELISA from NovaTec (currently for investigational research use).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be understood that the terms "comprise", "have", "include", and "contain" (and any related variants thereof) are open-ended linking verbs. As a result, a method, step, or device that "comprises", "has", "includes" or "contains" one or more steps or elements possesses those one or more steps or elements, but is not limited to possessing only those one or more steps or elements. The corresponding structures, materials, acts, and equivalents of all means or step plus function elements in the claims below, if any, are intended to include any structure, material, or act for performing the function in combination with other claimed elements as specifically claimed. The disclosure herein is illustrative and not intended to be exhaustive or limited to the invention in the form disclosed. Many modifications and variations will be apparent to those of ordinary skill in the art without departing from the scope and spirit of the invention. Embodiments are described to best explain the principles of one or more aspects of the invention and the practical application, and to enable others of ordinary skill in the art to understand one or more aspects of the invention for various embodiments with various modifications as are suited to the particular use contemplated. Further details pertaining to the present disclosure can be found in Appendix A, attached hereto and incorporated herein in its entirety.

REFERENCES

Calvet, G. A., Santos, F. B., and Sequeira, P. C. (2016). Zika virus infection: epidemiology, clinical manifestations and diagnosis. Curr Opin Infect Dis 29, 459-466.

Garcia, G., Vaughn, D. W., and Del Angel, R. M. (1997). Recognition of synthetic oligopeptides from nonstructural proteins NS1 and NS3 of dengue-4 virus by sera from dengue virus-infected children. American Journal of Tropical Medicine & Hygiene 56, 466-470.

Lanciotti, R. S., Kosoy, O. L., Laven, J. J., Velez, J. O., Lambert, A. J., Johnson, A. J., Stanfield, S. M., and Duffy, M. R. (2008). Genetic and serologic properties of Zika virus associated with an epidemic, Yap State, Micronesia, 2007. Emerg Infect Dis 14, 1232-1239.

Lindenbach, B. D., Murray, C. L., Thiel, H. J., Rice, C. M. (2013). Flaviviridae. In Fields Virology, 6th, Vol. 1, D. M. Knipe and P. M. Howley, eds. ((Philadelphia: Lippincott William & Wilkins), pp. 712-746).

Martin, D. A., Muth, D. A., Brown, T., Johnson, A. J., Karabatsos, N., and Roehrig, J. T. (2000). Standardization of immunoglobulin M capture enzyme-linked immunosorbent assays for routine diagnosis of arboviral infections. J Clin Microbiol 38, 1823-1826.

Musso, D., and Gubler, D. J. (2016). Zika Virus. Clin Microbiol Rev 29, 487-524.

Shan, C., Xie, X., Barrett, A. D. T., Garcia-Blanco, M. A., Tesh, R. B., Vasconcelos, P. F. d. C., Vasilakis, N., Weaver, S. C., and Shi, P.-Y. (2016a). Zika Virus: Diagnosis, Therapeutics, and Vaccine. ACS Infectious Diseases 2, 170-172.

Shan, C., Xie, X., Muruato, A. E., Rossi, S. L., Roundy, C. M., Azar, S. R., Yang, Y., Tesh, R. B., Bourne, N., Barrett, A. D., et al. (2016b). An Infectious cDNA Clone of Zika Virus to Study Viral Virulence, Mosquito Transmission, and Antiviral Inhibitors. Cell Host Microbe 19, 891-900.

Shu, P. Y., Chen, L. K., Chang, S. F., Yueh, Y. Y., Chow, L., Chien, L. J., Chin, C., Yang, H. H., Lin, T. H., and Huang, J. H. (2002). Potential application of nonstructural protein NS1 serotype-specific immunoglobulin G enzyme-linked immunosorbent assay in the seroepidemiologic study of dengue virus infection: correlation of results with those of the plaque reduction neutralization test. Journal of Clinical Microbiology 40, 1840-1844.

Stettler, K., Beltramello, M., Espinosa, D. A., Graham, V., Cassotta, A., Bianchi, S., Vanzetta, F., Minola, A., Jaconi, S., Mele, F., et al. (2016). Specificity, cross-reactivity, and function of antibodies elicited by Zika virus infection. Science 353, 823-826.

Weaver, S. C., Costa, F., Garcia-Blanco, M. A., Ko, A. I., Ribeiro, G. S., Saade, G., Shi, P. Y., and Vasilakis, N. (2016). Zika virus: History, emergence, biology, and prospects for control. Antiviral Res 130, 69-80.

Wong, S. J., Boyle, R. H., Demarest, V. L., Woodmansee, A. N., Kramer, L. D., Li, H., Drebot, M., Koski, R. A., Fikrig, E., Martin, D. A., et al. (2003). An immunoassay targeting nonstructural protein 5 to differentiate West Nile virus infection from dengue and St. Louis encephalitis virus infections, and form flavivirus vaccination. J Clin Microbiol 41, 4217-4223.

Zhao, H., Fernandez, E., Dowd, K. A., Speer, S. D., Platt, D. J., Gorman, M. J., Govero, J., Nelson, C. A., Pierson, T. C., Diamond, M. S., et al. (2016). Structural Basis of Zika Virus-Specific Antibody Protection. Cell 166, 1016-1027.

Zhao, Y., Soh, T. S., Chan, K. W., Fung, S. S., Swaminathan, K., Lim, S. P., Shi, P. Y., Huber, T., Lescar, J., Luo, D., et al. (2015). Flexibility of NS5 Methyltransferase-Polymerase Linker Region Is Essential for Dengue Virus Replication. J Virol 89, 10717-10721.

What is claimed is:

1. A method, comprising:
   (i) incubating
      (a) a first sample from a subject with a first plurality of populations of microspheres conjugated to viral antigens under a first condition, wherein
         the viral antigens conjugated to microspheres of each population of the first plurality of populations of microspheres differ from the viral antigens conjugated to microspheres of all other populations of microspheres of the first plurality of populations of microspheres, and
         the first condition permits high-affinity binding and low-affinity binding of antibodies in the first sample to the viral antigens, and (b) a second sample from the subject with a second plurality of populations of microspheres conjugated to viral antigens under a second condition, wherein the viral antigens conjugated to microspheres of each population of the second plurality of populations of microspheres differ from the viral antigens conjugated to microspheres of all other populations of microspheres of the second plurality of populations of microspheres, and the second condition permits high-affinity binding but not low-affinity binding of antibodies in the second sample to the viral antigens, and (ii) detecting an amount of antibodies bound to each population of the first plurality of populations of microspheres and to each population of the second plurality of populations of microspheres, wherein a first viral antigen comprises full-length Zika virus (ZIKV) NS1, a second viral antigen comprises full-length ZIKV envelope protein, and a third viral antigen comprises a Dengue virus (DENV) antigen wherein the DENV antigen is selected from DENV1 NS1, DENV2 NS1, DENV3 NS1, and DENV4 NS1.

2. The method of claim 1, wherein a fourth viral antigen is full-length ZIKV NS5.

3. The method of claim 1, wherein the second condition comprises incubating in the presence of from 7 M urea to 9 M urea.

4. The method of claim 1, wherein the second condition comprises incubating in the presence of 8 M urea.

5. The method of claim 2, wherein the second condition comprises incubating in the presence of from 7 M urea to 9 M urea.

6. The method of claim 2, wherein the second condition comprises incubating in the presence of 8 M urea.

7. The method of claim 1, wherein the first sample, the second sample, or both samples comprise blood, serum, plasma, saliva, tears, feces, semen, mucous, tissue, tissue homogenate, cellular extract, and spinal fluid.

8. The method of claim 2, wherein the first sample, the second sample, or both samples comprise blood, serum, plasma, saliva, tears, feces, semen, mucous, tissue, tissue homogenate, cellular extract, and spinal fluid.

9. The method of claim 1, wherein first sample and the second sample comprise serum.

10. The method of claim 2, wherein first sample and the second sample comprise serum.

* * * * *